United States Patent
Alla et al.

(10) Patent No.: US 9,573,910 B2
(45) Date of Patent: Feb. 21, 2017

(54) OXAZOLIDINONE ANTIBACTERIAL COMPOUND

(71) Applicant: Lee Pharma Limited, Hyderabad (IN)

(72) Inventors: Raghu Mitra Alla, Hyderabad (IN);
Ajay Kumar Dubey, Hyderabad (IN);
Srinivas Reddy Mallepalli, Hyderabad (IN); Ramakrishna Reddy Pongilati, Hyderabad (IN)

(73) Assignee: Lee Pharma Limited, Hyderabad (IN)

( * ) Notice: Subject to any disclaimer, the term of this patent is extended or adjusted under 35 U.S.C. 154(b) by 0 days.

(21) Appl. No.: 15/034,878

(22) PCT Filed: Jul. 28, 2014

(86) PCT No.: PCT/IN2014/000497
§ 371 (c)(1),
(2) Date: May 6, 2016

(87) PCT Pub. No.: WO2015/068173
PCT Pub. Date: May 14, 2015

(65) Prior Publication Data
US 2016/0272597 A1    Sep. 22, 2016

(30) Foreign Application Priority Data

Nov. 8, 2013 (IN) .......................... 5063/CHE/2013
May 5, 2014 (IN) .......................... 2254/CHE/2014

(51) Int. Cl.
*C07D 263/20* (2006.01)
*A61K 31/5377* (2006.01)

(52) U.S. Cl.
CPC ........ *C07D 263/20* (2013.01); *A61K 31/5377* (2013.01); *C07B 2200/07* (2013.01)

(58) Field of Classification Search
CPC .................................................. C07D 263/20
See application file for complete search history.

(56) References Cited

U.S. PATENT DOCUMENTS 5,688,792 A * 11/1997 Barbachyn ........... C07D 263/20
514/235.5
6,689,779 B2  2/2004 Lee et al.

FOREIGN PATENT DOCUMENTS

| WO | 01/94342 A1 | 12/2001 |
| WO | 2010/031769 A1 | 3/2010 |
| WO | 2015/068171 A1 | 5/2015 |

OTHER PUBLICATIONS

Babu, K. Chandra et al.: "A new and alternate synthesis of Linezolid: An antibacterial agent", Der Pharma Chemica, vol. 3, No. 4, 2011, pp. 219-226.

(Continued)

*Primary Examiner* — Matthew Coughlin
(74) *Attorney, Agent, or Firm* — The Webb Law Firm

(57) ABSTRACT

The invention relates to novel oxazolidinone compound. More particularly, the invention relates to novel [(S)—N-[[3-[4-fluoro-3-morpholino phenyl]-2-oxooxazolidin-5-yl] methyl] acetamide] compound of Formula-I which was disclosed in Indian Patent Application No. 5063/CHE/2013 and corresponding PCT/IN2014/000018. The compound is a broad spectrum antimicrobial agent effective against Multi-Drug Resistant *S. Maltophilia* pathogen and a large number of gram positive and gram negative pathogens. The compound has shown excellent biological activities against *S. Maltophilia* which has developed resistance against a large number of antibiotics including some of the known and widely used oxazolidinone derivatives.

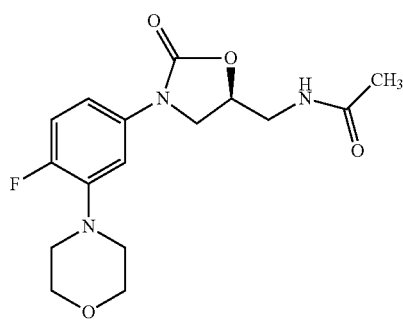

13 Claims, 9 Drawing Sheets

(56) References Cited

OTHER PUBLICATIONS

Ford, C. W. et al.: "The Discovery of linezolid, the first oxazolidinone antibacterial agent", Curr. Drug Targets Infect Disord, vol. 1, No. 2, Aug. 2001 (Aug. 1, 2001), pp. 181-199.
Lohray, Braj B. et al.: "A short synthesis of oxazolidinone derivatives linezolid and eperezolid: A new class of antibacterial", Tetrahedron Letters, vol. 40, No. Issue, Jun. 25, 1999 (Jun. 25, 1999), pp. 4855-4856.
Rajesh, Tammana et al.: "An expeditious construction of 3-aryl-5-(substituted methyl)-2-oxazolidinones: a short and efficient synthesis of Linezolid", ARKIVOC, vol. VI, 2012, pp. 45-56.
Rajesh, Tammana et al.: "A new and concise synthetic route to enantiopure Linezolid from (S)-epichlorohydrin", Der Pharma Chemica, vol. 3, No. 5, 2011, pp. 168-175.
Reddy, Pingili Krishna et al.: "A Novel Synthesis of Oxazolidinone Derivatives (A Key Intermediate of Linezolid", Oriental Journal of Chemistry, vol. 29, No. 3, 2013, pp. 1015-1019.
Xu, Guangyu et al.: "A Convenient Synthesis of Oxazolidine derivatives Linezolid and Eperezolid from (S)-Glyceraldehyde Acetonide", Heteroatom Chemistry, vol. 19, No. 3, 2008.
Yan-Wu Li et al.: "A facile synthesis of the oxazolidinone antibacterial agent linezolid", Chinese Chemical Letters, vol. 24, No. Issue, Mar. 2013 (Mar. 1, 2013), pp. 230-232.

\* cited by examiner

| 2θ | Intensity |
|---|---|
| 8.898 | 44.4 |
| 13.05 | 100.0 |
| 13.799 | 72.4 |
| 15.849 | 51.9 |
| 18.817 | 7.4 |
| 19.138 | 8.3 |
| 19.454 | 8.8 |
| 20.193 | 6.5 |
| 21.395 | 10.2 |
| 21.686 | 97.8 |
| 22.289 | 9.6 |
| 22.833 | 10.5 |
| 23.504 | 8.1 |
| 26.133 | 7.1 |
| 32.448 | 6.3 |

Figure 5A

OXAZOLIDINONE ANTIBACTERIAL COMPOUND

CROSS REFERENCE TO RELATED APPLICATIONS

This application is the national phase of PCT/IN2014/000497 and claims priority to Indian Patent Application No. 5063/CHE/2013 filed Nov. 8, 2013 and Indian Patent Application No. 2254/CHE/2014 filed May 5, 2014, the disclosures of which are hereby incorporated in their entirety by reference.

FIELD OF THE INVENTION

The invention relates to novel oxazolidinone compound. More particularly, the invention relates to novel [(S)—N-[[3-[4-fluoro-3-morpholino phenyl]-2-oxooxazolidin-5-yl] methyl] acetamide] compound of Formula-I which was disclosed in Indian Patent Application No. 5063/CHE/2013 and corresponding PCT/IN2014/000018. The compound is a broad spectrum antimicrobial agent effective against Multi-Drug Resistant S. Maltophilia pathogen and a large number of gram positive and gram negative pathogens. The compound has shown excellent biological activities against S. Maltophilia which has developed resistance against a large number of antibiotics including some of the known and widely used oxazolidinone derivatives.

Compound-I

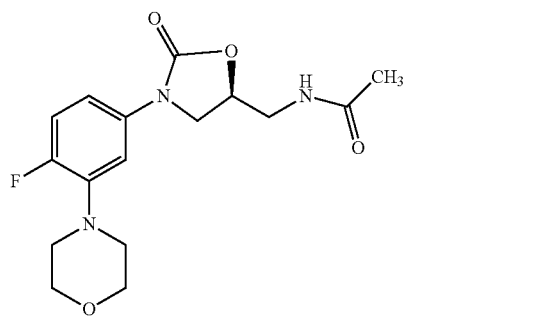

BACKGROUND OF THE INVENTION

Stenotrophomonas Maltophilia, commonly known as S. Maltophilia is an aerobic, gram negative emerging Multi-Drug Resistant global opportunistic pathogen. The increasing incidence of nosocomial and community-acquired S. Maltophilia infections is of particular concern for immunocompromised individuals, as this bacterial pathogen is associated with a significant fatality/case ratio and has emerged as an important nosocomial pathogen associated with crude mortality rates ranging from 14 to 69% in patients with bacteremia.

S. maltophilia exhibits resistance to a broad array of antibiotics, including TMP-SMX, β-lactam antibiotics, macrolides, cephalosporins, fluoroquinolones, aminoglycosides, carbapenems, chloramphenicol, tetracyclines, polymyxins, cefepime, ticarcillin-clavulanate, ceftazidime, and piperacillin-tazobactam.

Therefore S. Maltophilia is emerging as Multi-Drug Resistant pathogen worldwide, capable of causing serious respiratory tract infections, bloodstream and urinary infections. Some of the common infections caused by this notorious pathogen include pneumonia, blood stream infection, skin infection, surgical site related infections, urinary tract infections, endocarditis meningitis, intra-abdominal infections, co-morbid illness, endophthamitis and cystic fibrosis (a hereditary metabolic disorder of the exocrine glands that mainly affects the pancreas, respiratory system and sweat glands).

According to one study, the drug resistance of S. Maltophilia is increasing at the rate of 10% to 15% in USA and European countries making the treatment of S. Maltophilia infections significantly difficult with reduced treatment options.

Novel compound [(S)—N-[[3-[4-fluoro-3-morpholino phenyl]-2-oxooxazolidin-5-yl] methyl] acetamide] of Formula-I was disclosed in Indian Patent Application No. 5063/CHE/2013 and corresponding PCT/IN2014/000018 of the applicant which are incorporated herein by reference. This compound belongs to the oxazolidinone class of drugs which are known to have potent antimicrobial activity against a number of human and veterinary pathogens, including anaerobic organisms such as bacteroides and clostridia species and acid fast organisms such as mycobacterium tuberculosis and mycobacterium avium, multi-drug resistant Gram-positive bacteria, including methicillin resistant Staphylococcus aureus (MRSA), Staphylococcus epidermitis (MRSE), penicillin-resistant Streptococcus pneunoniae (PRSP) and vancomycin-resistant enterococci (VRE).

The oxazolidinones class of antibacterials possess a unique mechanism of inhibiting bacterial protein synthesis. Linezolid is one of the most important oxazolidinone class of drug having potent antibacterial activity and was the first oxazolidinone to be approved for clinical use with potential antibacterial activity against many important resistant pathogens. However, S. Maltophilia has exhibited resistance against Linezolid also and therefore, inventors were looking towards development of new antibacterial compound which could be effective against the S. Maltophilia and other Multi-Drug Resistant pathogens.

The inventors have developed a novel compound [(S)—N-[[3-[4-fluoro-3-morpholino phenyl]-2-oxooxazolidin-5-yl] methyl] acetamide] of Formula-I which was disclosed in Indian Patent Application No. 5063/CHE/2013 and corresponding PCT/IN2014/000018. In further antimicrobial studies on compound-I, it was observed that this compound had shown immense potential to treat the infections caused by the Multi-Drug Resistant S. Maltophilia pathogen and against a broad spectrum of gram positive and gram negative pathogens and has also shown promising results in Single Dose Acute Toxicity tests conducted on this compound. The compound has shown excellent biological activities against S. Maltophilia which has developed resistance against a large number of antibiotics including some of the known and widely used oxazolidinone derivatives.

OBJECT OF THE INVENTION

The primary object of the invention is to provide an antibiotic therapy for the treatment of Multi-Drug Resistant S. Maltophilia infections.

Another object of the invention is to provide a novel antibacterial for the treatment of infections caused by Multi-Drug Resistant S. Maltophilia and other drug resistant pathogens.

Another object of the invention is to provide a novel broad spectrum oxazolidinone derivative for the treatment of the infections caused by Multi-Drug Resistant *S. Maltophilia* and other gram positive and gram negative pathogens.

Another object of the invention is to provide a novel antibacterial compound and its pharmaceutically acceptable salts.

A further object of the invention is to provide a pharmaceutical composition of novel antibacterial for human and veterinary use.

SUMMARY OF THE INVENTION

Novel oxazolidinone compound [(S)—N-[[3-[4-fluoro-3-morpholino phenyl]-2-oxooxazolidin-5-yl] methyl] acetamide] of Formula-I was disclosed in Indian Patent Application No. 5063/CHE/2013 and corresponding PCT/IN2014/000018 of the applicant which are incorporated herein by reference.

Compound-I

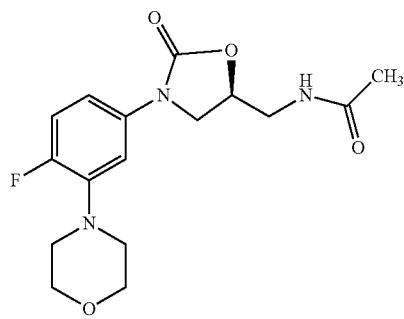 [SMILES: CC(=O)NC[C@H]1CN(c2ccc(F)c(N3CCOCC3)c2)C(=O)O1]

The compound of formula-I is characterized by following $^1$H-NMR, C13-NMR, Mass and IR spectral data.

IR Spectral Data:
3335, 3085, 2984, 2900, 2743, 2697, 1736, 1671, 1609, 1597, 1542, 1512, 1474, 1420, 1369, 1348, 1318, 1285, 1231, 1142, 1114, 1083. (As shown in FIG. 1)
(H-NMR:CDCl$_3$: δ 2.01 (s, 3H), 3.06 (t, 4H), 3.60-3.78 (m, 4H), 3.85-3.86 (t, 2H), 4.03 (t, 2H), 4.78 (m, 1H), 6.12 (s, 1H), 6.82-6.85 (m, 1H), 6.98-7.03 (q, 1H), 7.32-7.34 (dd, 1H) (As shown in FIG. 2)
$^{13}$C-NMR:CDCl$_3$: 22.7, 41.7, 47.7, 50.5, 66.6, 71.8, 109.6, 111.9, 116.2, 134.3, 139.9, 140.0, 150.8, 153.2, 154.6, 171.2. (As shown in FIG. 3)
ESI-MS (m/z): 338.37 (M+1) (As shown in FIG. 4)
The compound of formula-I is further characterized by XRD spectrum of 8.898, 13.05, 13.799, 15.849, 18.817, 19.138, 19.454, 20.193, 21.395, 21.686, 22.289, 22.833, 23.504, 26.133 and 32.448 degrees 2 theta. (as shown in FIG. 5).

The compound-I is prepared by a process comprising the steps of
a) reduction of 3,4-difluoro nitrobenzene compound of formula-II Compound-II

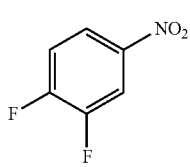

to give 3,4-difluoro-aniline compound of formula-III;

Compound-III

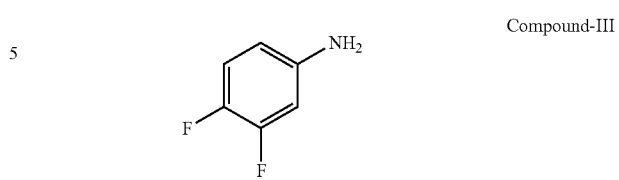

b) reacting compound-III with (R) epichlorohydrin to give (R)-1-chloro-3-((3,4-difluorophenyl)amino)propan-2-ol compound of formula-IV;

Compound-IV

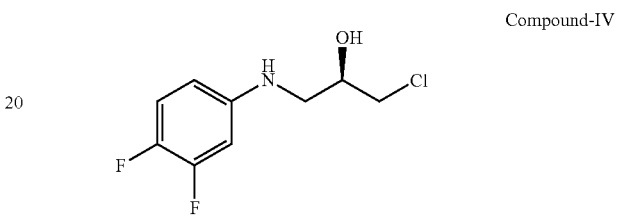

c) coupling (R)-1-chloro-3-((3,4-difluorophenyl)amino)propan-2-ol compound of formula-IV with Potassium phthalimide to obtain (R)-2-(3-((3,4-difluorophenyl)amino)-2-hydroxyl propyl)isoindoline-1,3-dione compound of formula-V;

Compound-V

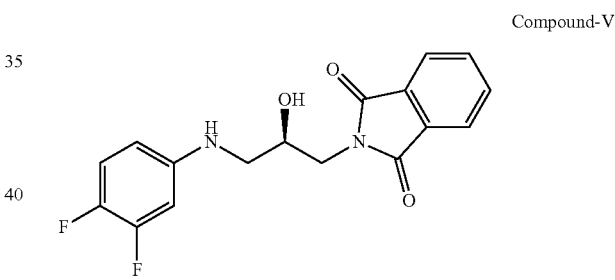

d) cyclization of (R)-2-(3-((3,4-difluorophenyl)amino)-2-hydroxyl propyl) isoindoline-1,3-dione compound of formula-V with CDI to obtain (S)-2-((3-(3,4-difluorophenyl)-2-oxooxazolidin-5-yl)methyl)isoindoline-1,3-dione compound of formula-VI;

Compound-VI

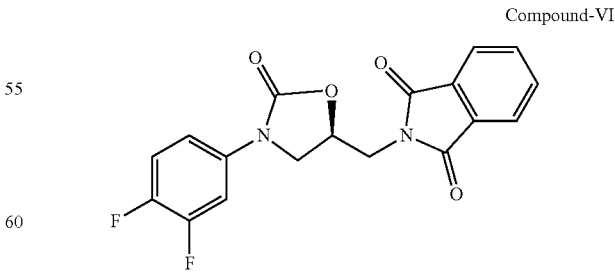

e) opening of phthalimide ring of compound-VI by reacting with Hydrazine hydrate to obtain (S)-5-(amino methyl)-3-(3,4-difluorophenyl)oxazolidin-2-one compound of formula-VII;

Compound-VII

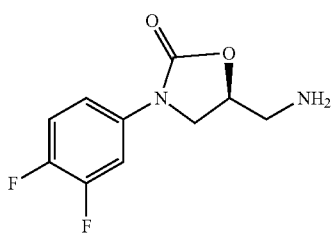

f) acylation of compound-VII with Acetic anhydride to obtain the corresponding (S)—N-((3-(3,4-difluorophenyl)-2-oxooxazolidin-5-yl)methyl)acetamide compound of formula-VIII;

Compound-VIII

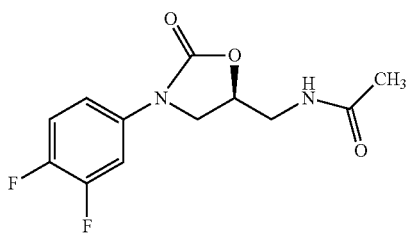

g) nitration of compound VIII with nitrating reagents (nitric acid & sulphuric acid) to give (S)—N-((3-(4,5-difluoro-2-nitrophenyl)-2-oxooxazolidin-5-yl) methyl)acetamide compound of formula IX;

Compound-IX

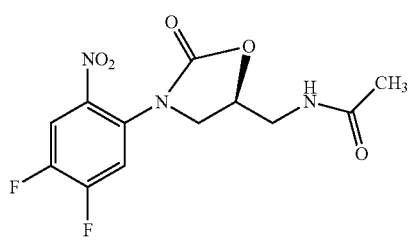

h) reacting (S)—N-((3-(4,5-difluoro-2-nitrophenyl)-2-oxooxazolidin-5-yl) methyl) acetamide compound-IX with morpholine to give (S)—N-((3-(4-fluoro-5-morpholino-2-nitrophenyl)-2-oxooxazolidin-5-yl)methyl)acetamide compound formula-X;

Compound-X

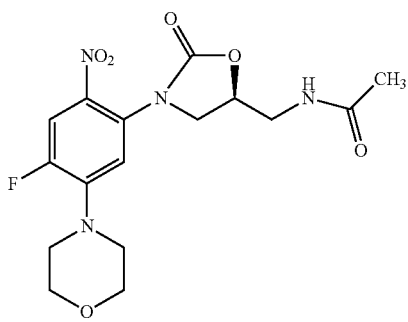

i) reduction of (S)—N-((3-(4-fluoro-5-morpholino-2-nitrophenyl)-2-oxooxazolidin-5-yl)methyl)acetamide compound of formula-X to obtain (S)—N-((3-(2-amino-4-fluoro-5-morpholinophenyl)-2-oxooxazolidin-5-yl) methyl)acetamide formula XI;

Compound-XI

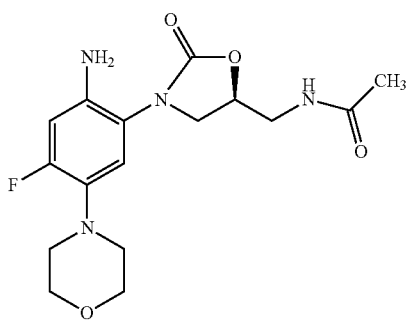

j) deamination of (S)—N-((3-(2-amino-4-fluoro-5-morpholinophenyl)-2-oxooxazolidin-5-yl)methyl)acetamide (compound-XI) to obtain (S)—N-((3-(4-fluoro-3-morpholinophenyl)-2-oxooxazolidin-5-yl)methyl)acetamide compound of formula-I.

Compound-I

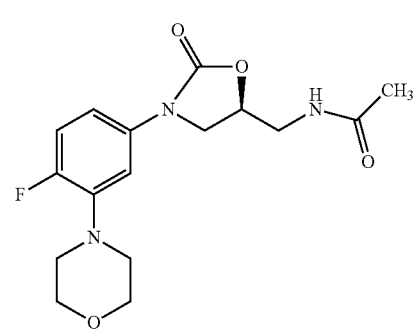

To ascertain the antibacterial activities of the compound-I, a thorough antimicrobial study was performed and its coverage spectrum as well as bacteriostatic and bactericidal activities were studied.

The biological activity test of Compound-I was conducted at INDIAN INSTITUTE OF CHEMICAL TECHNOLOGY (IICT) Hyderabad, which revealed promising results against the drug resistant *S. Maltophilia* pathogen as well as other gram positive and gram negative pathogens such as *M. luteus, B. sterothemophilus, P. putida, K. pneumonia, P. aeruginosa, E. coli, P. vulgaris, S. typhi, B. subtilis, S. mutans, B. sphaericus, B. circulans, Lysinobacillus, B. cereus, B. megatherium, P. mirabilis* and *S. paratyphi*.

Anti bacterial evaluation of compound-I was done against *Stenotrophomonas maltophilia* on following parameters—
  a. Agar-plate assay for different concentrations (10, 50, 100, 150 μg)
  b. MIC studies
    1. With different concentrations (1000 to 5 μg/ml—~10 different concentrations)
    2. Different time periods (4 to 32 hrs—8 different time intervals)
  c. Mode of action with relation to survivability of organism 1. Cidal/static with concentration and incubation time based)
2. Evaluation by colony counting/dye based
d. Susceptibility test (evaluation of >40 antibiotics of different nature)
e. Antibacterial potential studies with other infectious bacteria (~20 different strains)

The Antimicrobial activity of compound-I revealed that—
compound-I is active against *S. maltophilia* while Linezolid and Vancomycin are not inhibitory
Concentration based inhibitory activity was noticed against *S. maltophilia*
MIC studies suggested 500 and above µg/ml is effective for complete inhibition (bacteriocidal) of *S. maltophilia*
Concentration <500 µg acts as bacteriostatic till 24 hours
The antibiotic susceptibility profile of *S. maltophilia* was explored
compound-I is effective against Xanthomonadaceae (*S. maltophilia* and *Pseudomonas* sp.) & some species of *Bacillus* (*Bacillus cereus*) family members During lab analysis it was found that at 10 µg level the compound-I is effective in growth inhibition of *S. maltophilia*. Also increase of compound-I concentration resulted in increased zone of growth inhibition. However, proportionate growth inhibition zone was not noticed with increase of compound-I concentration on agar plate assay.

It was observed that low dose of compound-I is sufficient to reduce the growth of *S. maltophilia*. Although, the observation of un-proportionate inhibition zone Vs concentration of compound-I is interesting fact. This may be attributed to mass transfer of compound-I in agar during experimentation which influences the drug and microbial interaction. One of the alternatives to reduce the influence of mass transfer and improve the contact between compound-I and microbial strain was removal of solid barrier or increasing the diffusion of compound in the medium by broth dilution method.

To understand the antimicrobial potential of compound-I, initial lab experiments were planned to evaluate comparative microbial growth inhibition zone against Linezolid and Vancomycin using twenty different bacterial strains consisting of gram-positive and gram-negative nature. The selection of vancomycin for comparison was based on the fact that it is an alternative antibiotic which is generally used for treating the gram-positive bacterial infections. Among all tested different microbial strains, *S. maltophilia*, *P. aeruginosa* and one of the strains of *B. cereus* showed anti bacterial activity against compound-I, but not vancomycin or Linezolid, suggesting compound-I, could be a potential drug candidate to control the infections associated with above organisms more effectively. It is also established from the lab analysis that compound-I is effective against Xanthomonadaceae (*S. maltophilia* and *Pseudomonas* sp.) & some species of *Bacillus* (*Bacillus cereus*) family members.

BRIEF DESCRIPTION OF THE DRAWINGS

FIGS. 5A and 5B are XRD data of Oxazolidinone compound of formula-I.

DETAILED DESCRIPTION OF THE INVENTION

Detailed embodiments of the present invention are disclosed herein below. However, it is to be understood that the disclosed embodiments are merely exemplary of the invention, which can be embodied in various forms. The scope of the invention is not limited to the disclosed embodiments and terms and phrases used herein are not intended to be limiting but rather to provide an understandable description of the invention. The invention is defined by claims appended hereto.

Novel oxazolidinone compound [(S)—N-[[3-[4-fluoro-3-morpholino phenyl]-2-oxooxazolidin-5-yl] methyl] acetamide] of Formula-I was disclosed in Indian Patent Application No. 5063/CHE/2013 and corresponding PCT/IN2014/000018 which are incorporated herein by reference.

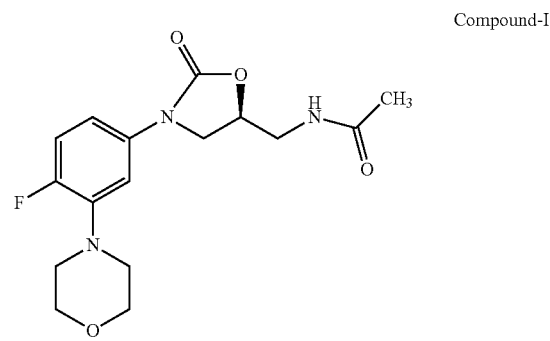 [SMILES: CC(=O)NC[C@H]1CN(c2ccc(F)c(N3CCOCC3)c2)C(=O)O1]

Compound-I

Figure 1:
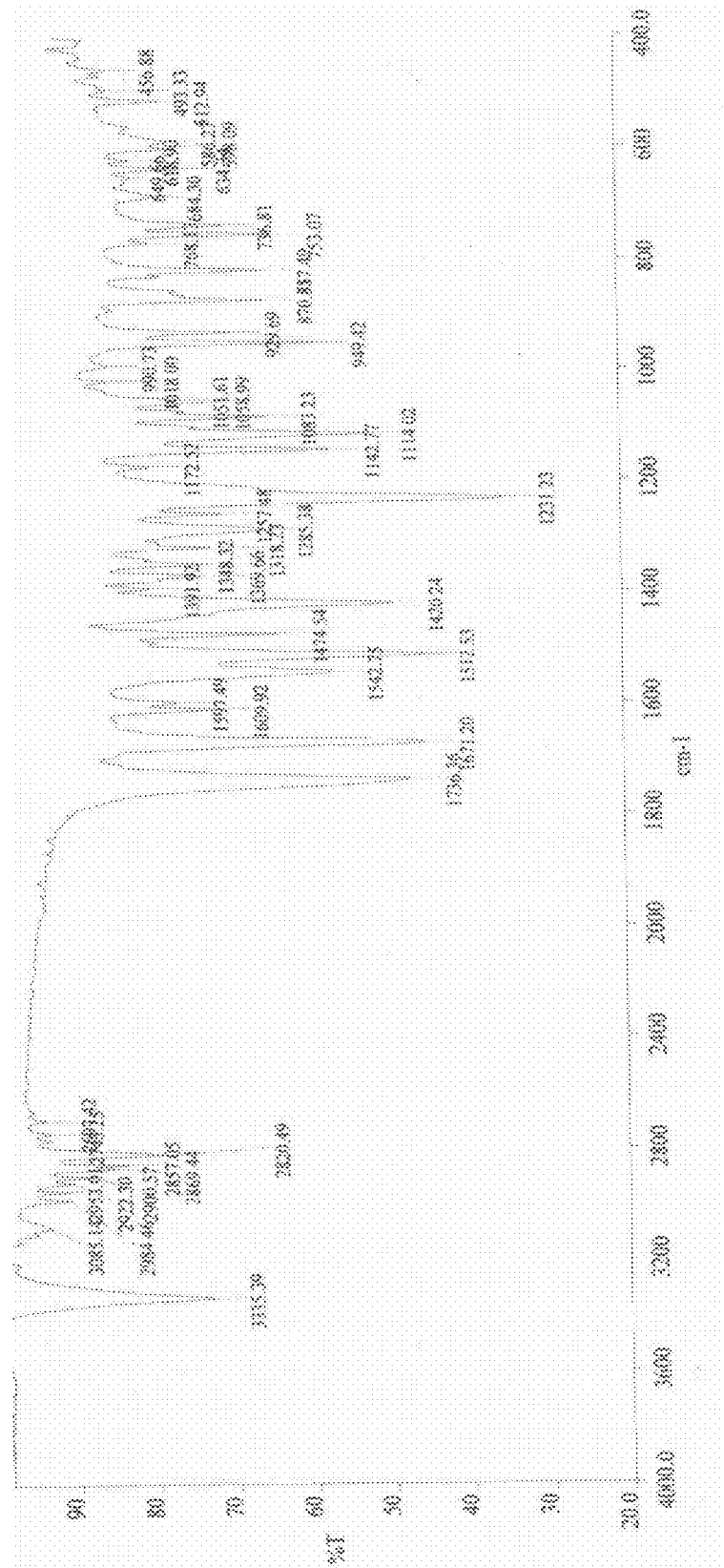
FIG. 1 is IR Spectral data of Oxazolidinone compound of formula-I.
Figure 2:
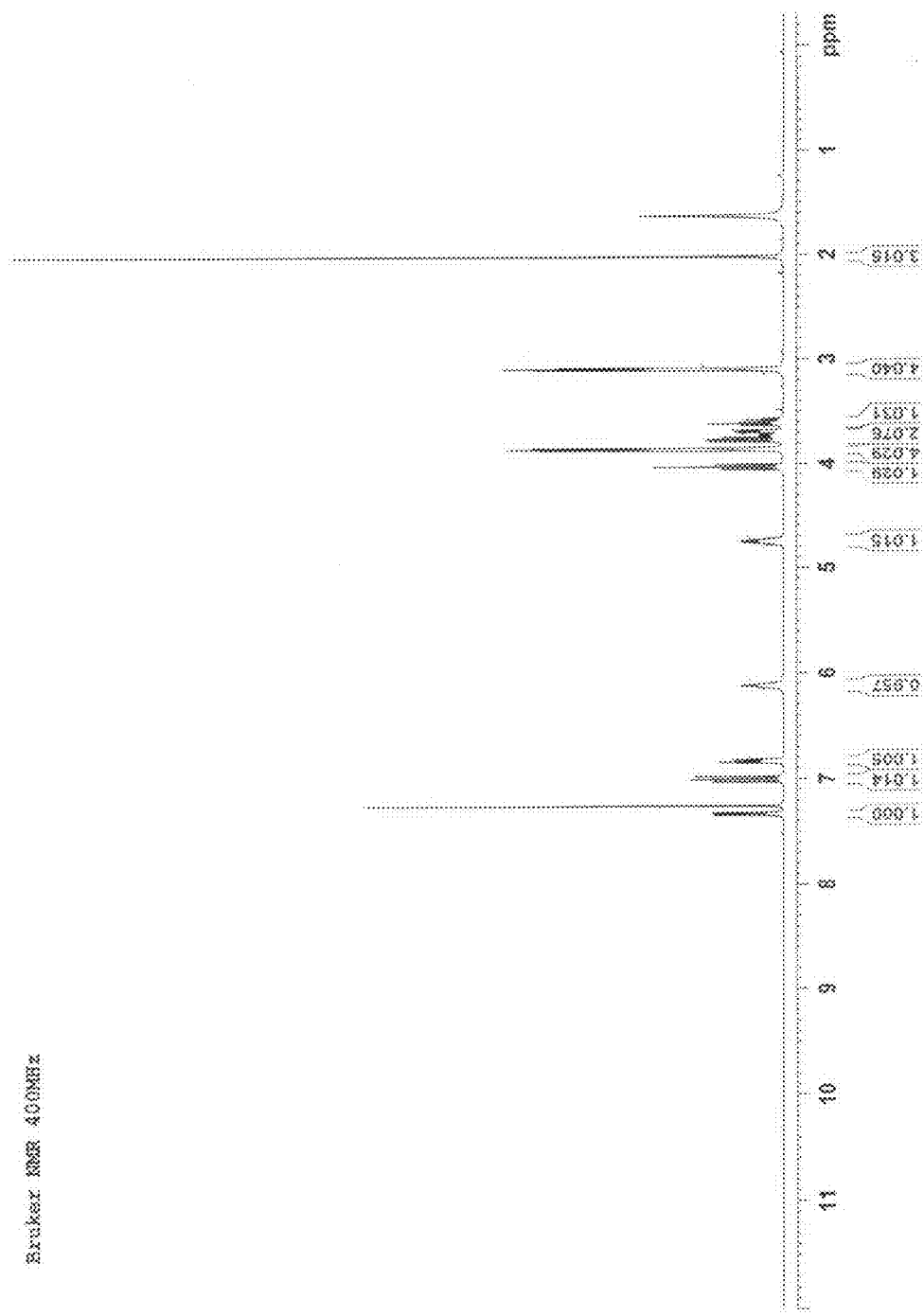
FIG. 2 is H-NMR Spectral data of Oxazolidinone compound of formula-I.
Figure 3:
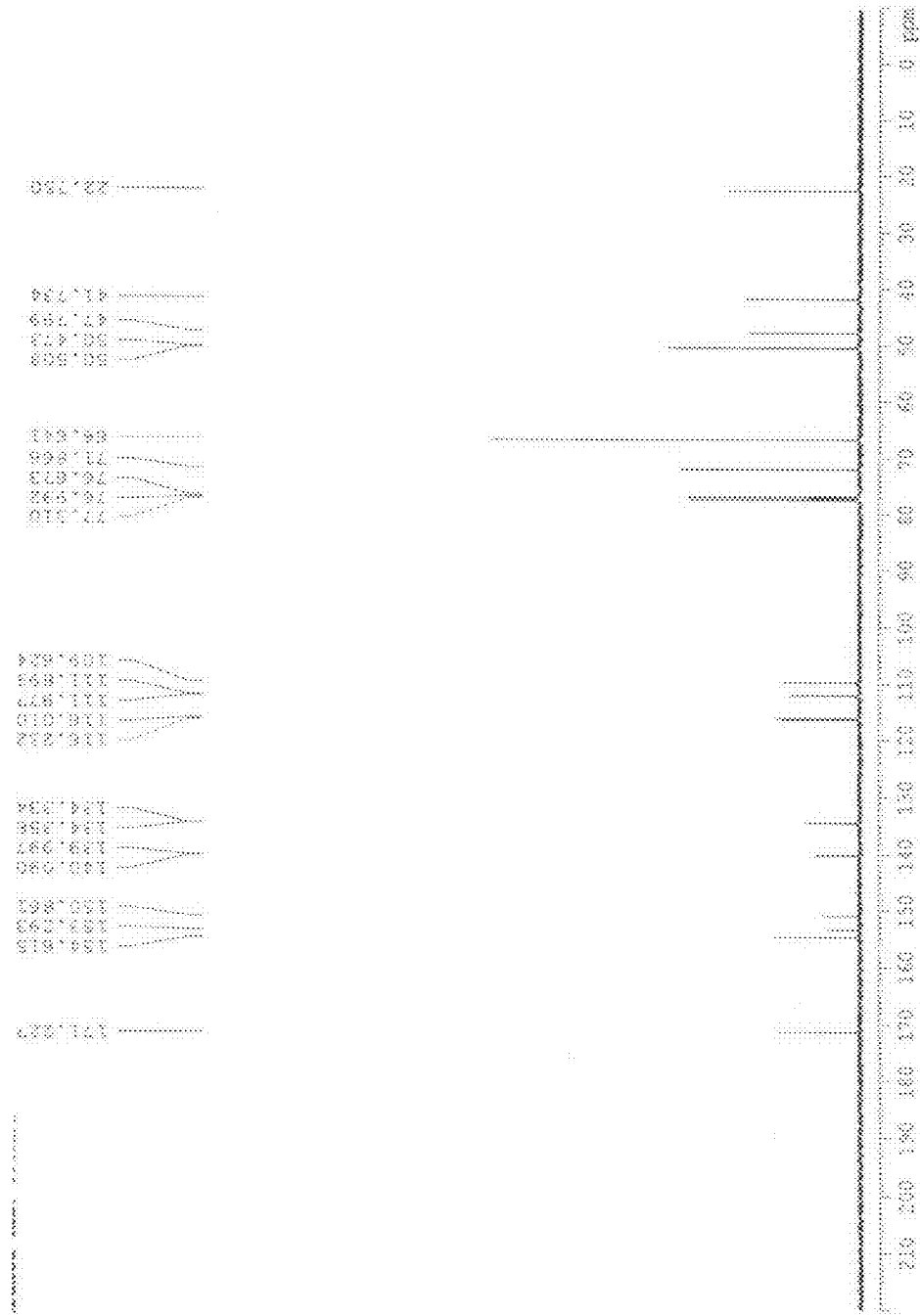
FIG. 3 is $^{13}$C-NMR Spectral data of Oxazolidinone compound of formula-I.
Figure 4:
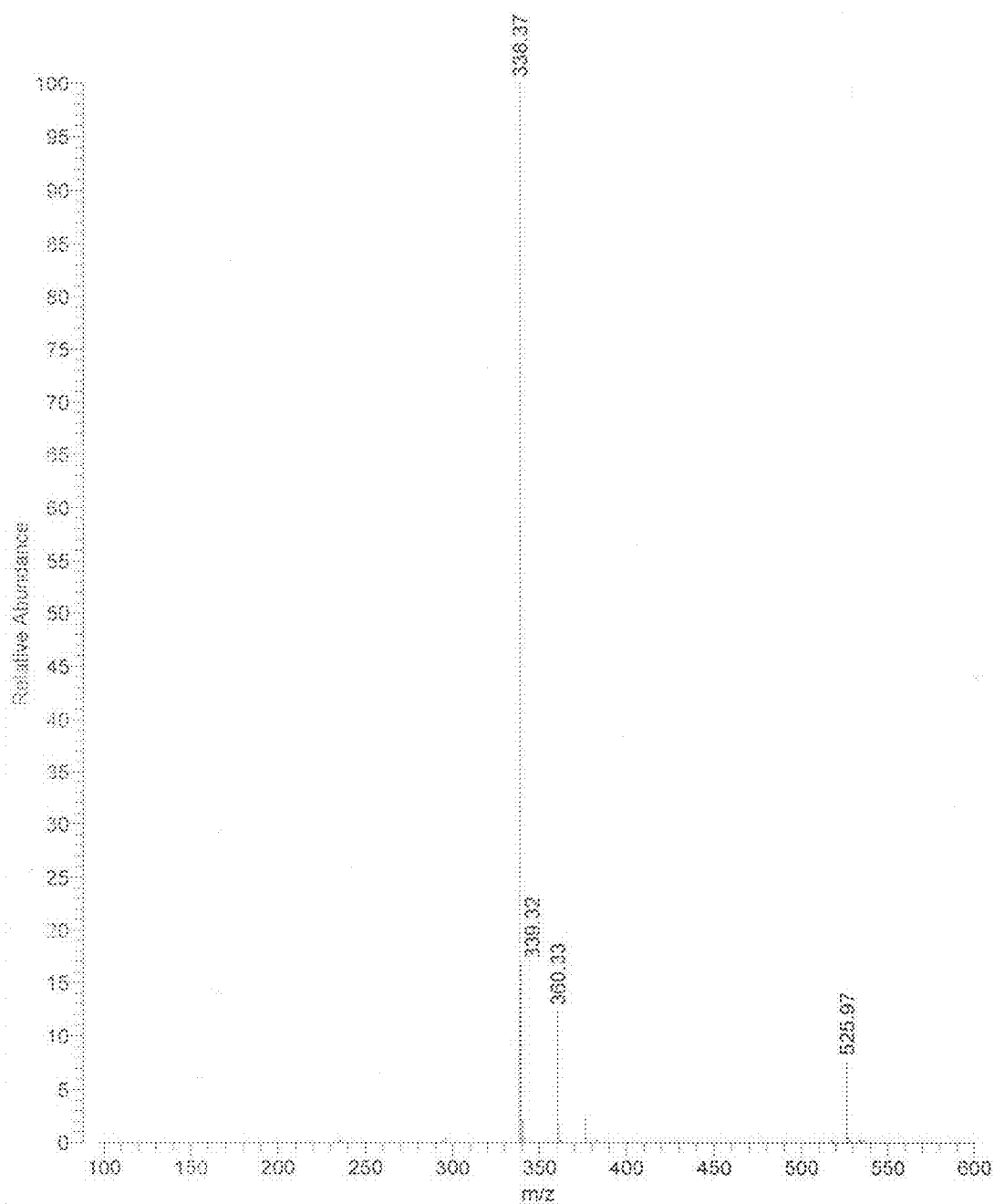
FIG. 4 is ESI-MS (m/z) spectral data of Oxazolidinone compound of formula-I.
Figure 5B:
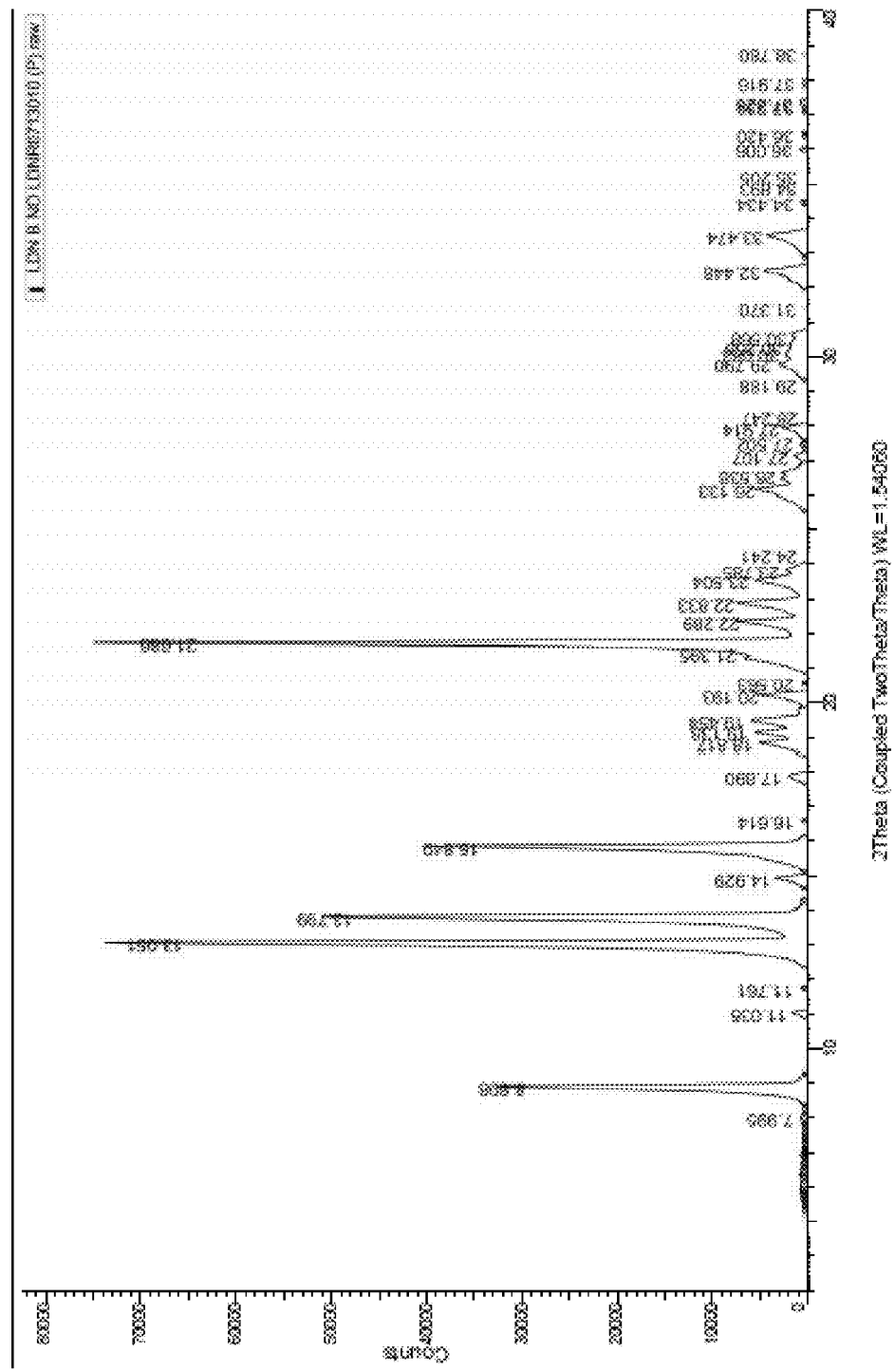

The compound of formula-I is characterized by following $^1$H-NMR, C13-NMR, Mass and IR spectral data.
IR Spectral Data:
3335, 3085, 2984, 2900, 2743, 2697, 1736, 1671, 1609, 1597, 1542, 1512, 1474, 1420, 1369, 1348, 1318, 1285, 1231, 1142, 1114, 1083. (As shown in FIG. 1)
(H-NMR:CDCl$_3$: δ 2.01 (s, 3H), 3.06 (t, 4H), 3.60-3.78 (m, 4H), 3.85-3.86 (t, 2H), 4.03 (t, 2H), 4.78 (m, 1H), 6.12 (s, 1H), 6.82-6.85 (m, 1H), 6.98-7.03 (q, 1H), 7.32-7.34 (dd, 1H) (As shown in FIG. 2)
$^{13}$C-NMR:CDCl$_3$: 22.7, 41.7, 47.7, 50.5, 66.6, 71.8, 109.6, 111.9, 116.2, 134.3, 139.9, 140.0, 150.8, 153.2, 154.6, 171.2. (As shown in FIG. 3)
ESI-MS (m/z): 338.37 (M+1) (As shown in FIG. 4)
The compound of formula-I is further characterized by XRD spectrum of 8.898, 13.05, 13.799, 15.849, 18.817, 19.138, 19.454, 20.193, 21.395, 21.686, 22.289, 22.833, 23.504, 26.133 and 32.448 degrees 2 theta. (as shown in FIG. 5).
The process of synthesis of the novel oxazolidinone compound of Formula-I is illustrated in below scheme-I:

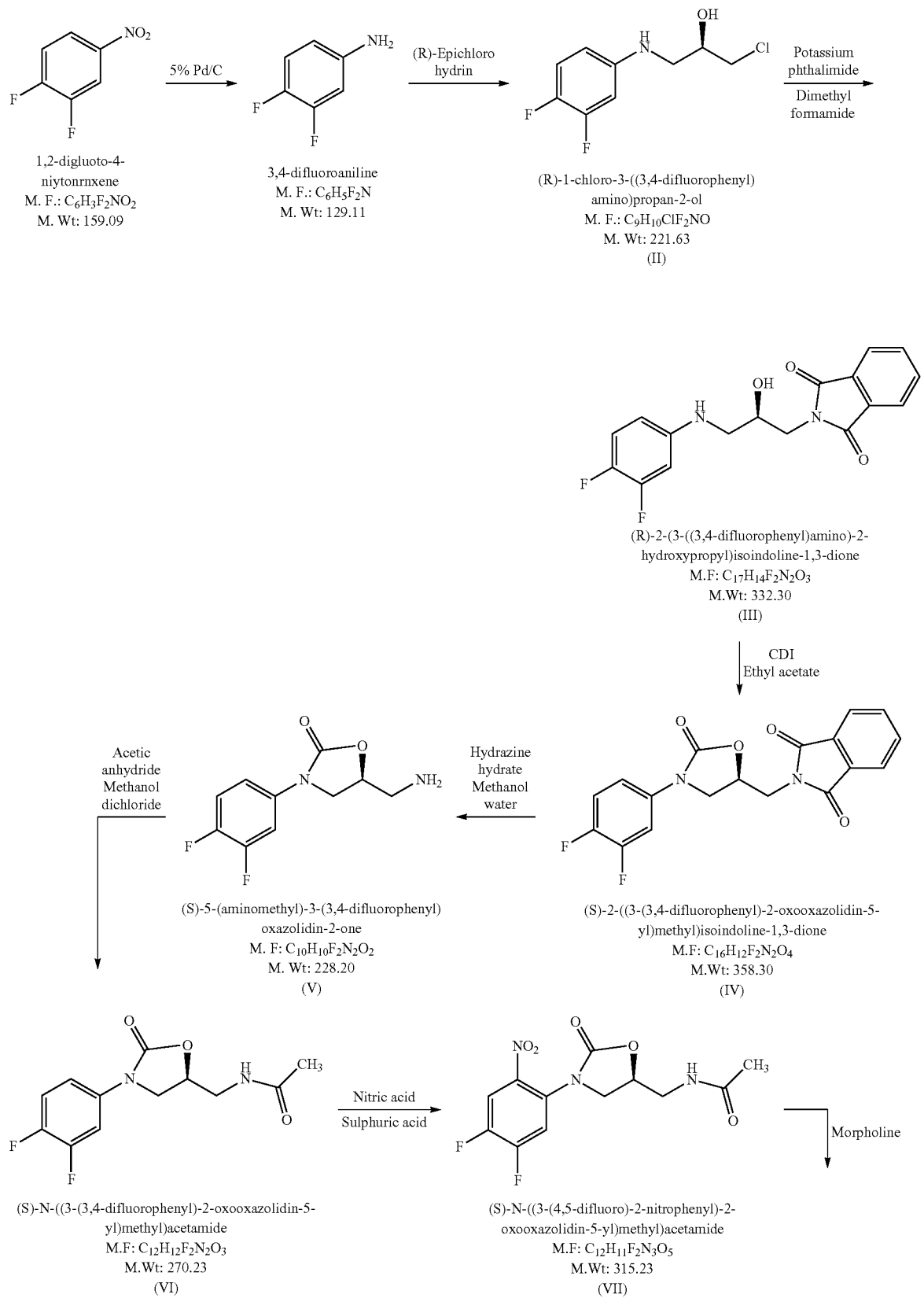

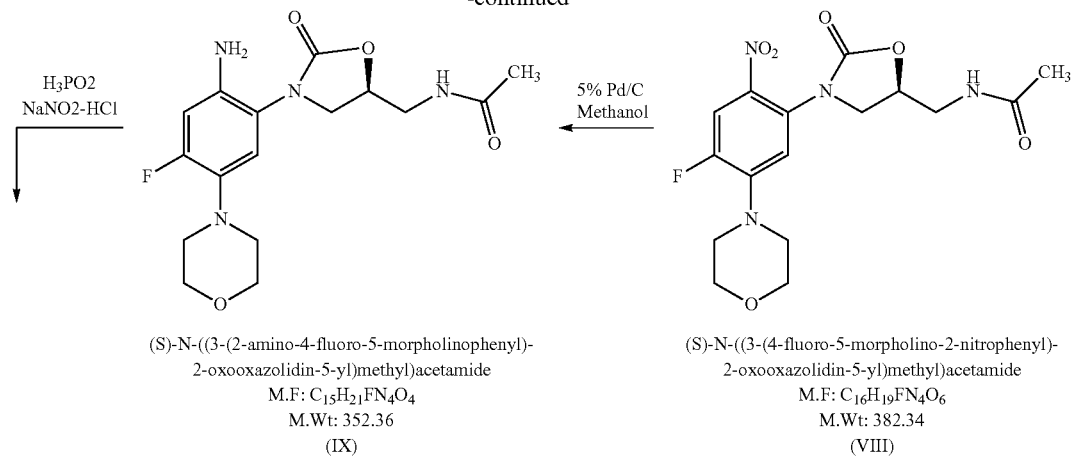

(S)-N-((3-(2-amino-4-fluoro-5-morpholinophenyl)-
2-oxooxazolidin-5-yl)methyl)acetamide
M.F: $C_{15}H_{21}FN_4O_4$
M.Wt: 352.36
(IX)

(S)-N-((3-(4-fluoro-5-morpholino-2-nitrophenyl)-
2-oxooxazolidin-5-yl)methyl)acetamide
M.F: $C_{16}H_{19}FN_4O_6$
M.Wt: 382.34
(VIII)

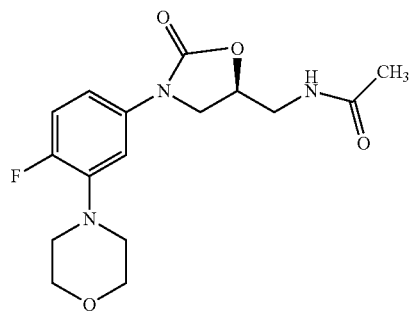

(S)-N-((3-(4-fluoro-3-morpholinophenyl)-
2-oxooxazolidin-5-yl)methyl)acetamide
M.F: $C_{16}H_{20}FN_3O_4$
M.Wt: 337.35
Formula-I The process for synthesis of the novel oxazolidinone compound [(S)—N-[[3-[4-fluoro-3-morpholino phenyl]-2-oxooxazolidin-5-yl] methyl] acetamide] (formula-I) comprises the following steps:

a) reduction of 3,4-difluoro nitrobenzene compound of formula-II

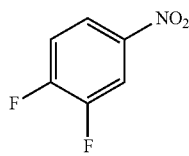

Compound-II to give 3,4-difluoro-aniline compound of formula-III;

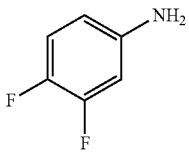

Compound-III b) reacting compound-III with (R) epichlorohydrin to obtain (R)-1-chloro-3-((3,4-difluorophenyl)amino)propan-2-ol compound of formula-IV;

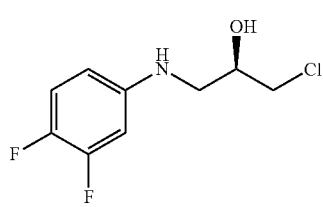

Compound-IV c) coupling the (R)-1-chloro-3-((3,4-difluorophenyl)amino) propan-2-ol compound of formula-IV with Potassium phthalimide to obtain (R)-2-(3-((3,4-difluorophenyl)amino)-2-hydroxyl propyl)isoindoline-1,3-dione compound of formula-V;

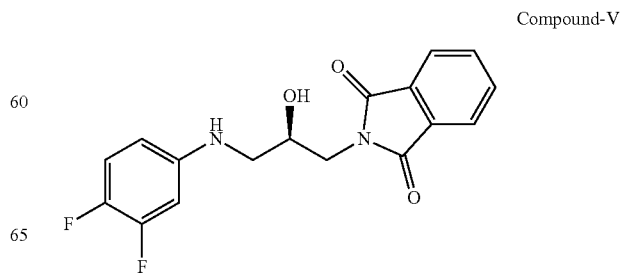

Compound-V d) cyclization of (R)-2-(3-((3,4-difluorophenyl)amino)-2-hydroxyl propyl) isoindoline-1,3-dione compound of formula-V with CDI to obtain (S)-2-((3-(3,4-difluorophenyl)-2-oxooxazolidin-5-yl)methyl)isoindoline-1,3-dione compound of formula-VI;

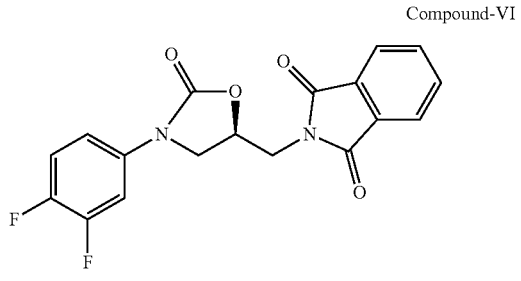 [SMILES: O=C1c2ccccc2C(=O)N1C[C@H]1CN(c2ccc(F)c(F)c2)C(=O)O1]

Compound-VI e) opening of phthalimide ring of compound-VI by reacting with Hydrazine hydrate to obtain (S)-5-(amino methyl)-3-(3,4-difluorophenyl)oxazolidin-2-one compound of formula-VII;

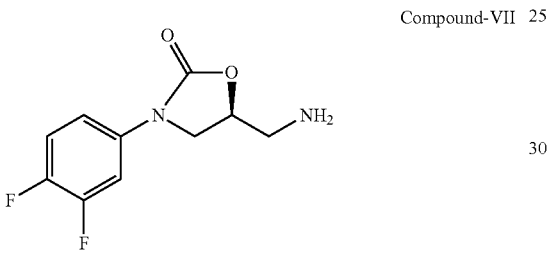

Compound-VII f) acylation of compound-VII with Acetic anhydride to obtain the corresponding (S)—N-((3-(3,4-difluorophenyl)-2-oxooxazolidin-5-yl)methyl)acetamide compound of formula-VIII;

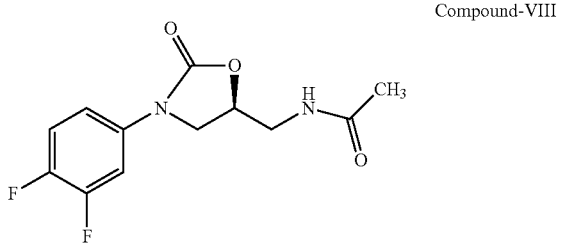 [SMILES: CC(=O)NC[C@H]1CN(c2ccc(F)c(F)c2)C(=O)O1]

Compound-VIII g) nitration of compound VIII with nitrating reagents (nitric acid & sulphuric acid) to give (S)—N-((3-(4,5-difluoro-2-nitrophenyl)-2-oxooxazolidin-5-yl) methyl)acetamide compound of formula IX;

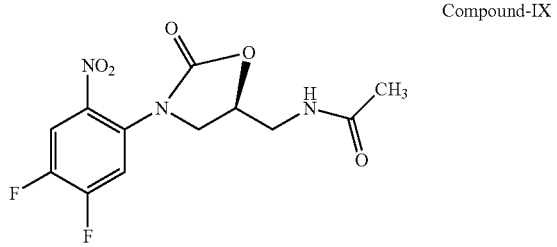 [SMILES: CC(=O)NC[C@H]1CN(c2cc(F)c(F)cc2[N+](=O)[O-])C(=O)O1]

Compound-IX h) reacting (S)—N-((3-(4,5-difluoro-2-nitrophenyl)-2-oxooxazolidin-5-yl) methyl) acetamide compound-IX with morpholine to give (S)—N-((3-(4-fluoro-5-morpholino-2-nitrophenyl)-2-oxooxazolidin-5-yl)methyl)acetamide compound formula-X;

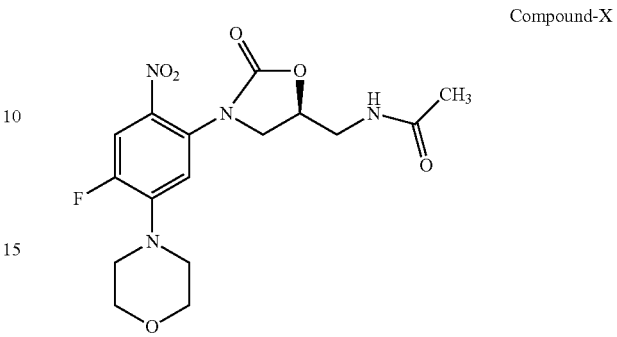

Compound-X i) reduction of (S)—N-((3-(4-fluoro-5-morpholino-2-nitrophenyl)-2-oxooxazolidin-5-yl)methyl)acetamide compound of formula-X to obtain (S)—N-((3-(2-amino-4-fluoro-5-morpholinophenyl)-2-oxooxazolidin-5-yl)methyl)acetamide formula XI;

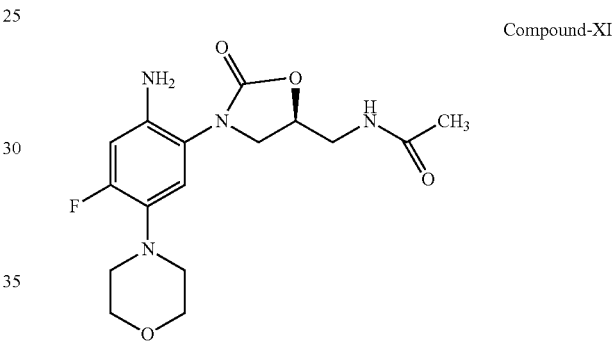

Compound-XI j) deamination of (S)—N-((3-(2-amino-4-fluoro-5-morpholinophenyl)-2-oxooxazolidin-5-yl)methyl)acetamide (compound-XI) to obtain (S)—N-((3-(4-fluoro-3-morpholinophenyl)-2-oxooxazolidin-5-yl)methyl)acetamide compound of formula-I.

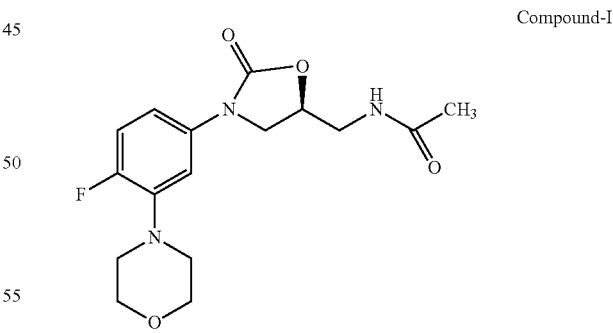

Compound-I

Each step of the above process is further elaborated herein below.

Step-a: Reduction of 3,4-difluoro nitrobenzene to give 3,4-difluoro-anilene 3,4-difluoro nitrobenzene of formula-I is reduced with pd/C in autoclave, applying Hydrogen gas and maintaining the reaction for 3-4 hrs. After completion of reaction it is filtered and distilled to obtain compound of formula-III.

Step-b: Reaction of 3,4-difluoro-anilene with (R) epichlorohydrin to Yield (R)-1-chloro-3-((3,4-difluorophenyl)amino)propan-2-ol of Formula-IV This step involves reacting 3,4-Difluoro aniline with (R) epichlorohydrin, heating at 50° C.-55° C. 5.0-6.0 hrs and after completion of reaction distilled under vacuum to obtain (R)-1-chloro-3-((3,4 difluorophenyl)amino)propan-2-ol of formula-IV.

Step-c: Coupling (R)-1-chloro-3-((3,4-difluorophenyl)amino)propan-2-ol of Formula-IV with Potassium phthalimide to Yield (R)-2-(3-((3,4-difluorophenyl)amino)-2-hydroxyl propyl)isoindoline-1,3-dione of Formula-V In this step (R)-1-chloro-3-((3,4-difluorophenyl)amino) propan-2-ol of formula-IV is treated with Potassium phthalimide in DMF at 140-150° C. for 5.0-6.0 hrs. Then cooled, filtered and washed with mixture of water and methanol to yield (R)-2-(3-((3,4-difluorophenyl)amino)-2-hydroxyl propyl)isoindoline-1,3-dione of formula-V.

Step-d: Cyclization of (R)-2-(3-((3,4-difluorophenyl)amino)-2-hydroxyl propyl) isoindoline-1,3-dione of Formula-V with CDI to Yield (S)-2-((3-(3,4-difluorophenyl)-2-oxooxazolidin-5-yl)methyl) isoindoline-1,3-dione of formula-VI In this step (R)-2-(3-((3,4-difluorophenyl)amino)-2-hydroxypropyl) isoindoline-1,3-dione (formula-V) in ethyl acetate is cyclized with CDI, stirred for 3.0-4.0 hrs at room temperature. After completion of reaction washed with ethyl acetate followed by washed with water to get (S)-2-((3-(3, 4-difluorophenyl)-2-oxooxazolidin-5-yl)methyl)isoindoline-1,3-dione of formula-VI.

Step-e: Opening of Phthalimide Ring of (S)-2-((3-(3,4 difluorophenyl)-2-oxooxazolidin-5-yl)methyl) isoindoline-1,3-dione by Reacting with Hydrazine Hydrate to Yield (S)-5-(amino methyl)-3-(3,4 difluorophenyl)oxazolidin-2-one. of Formula-VII This step involves reaction of (S)-2-((3-(3,4-difluorophenyl)-2-oxooxazolidin-5-yl)methyl)isoindoline-1,3-dione with Hydrazine hydrate in methanol and water at room temperature and heated to 65-70° C., stirred for 2.0-3.0 hrs same temperature. After completion of reaction extracted with dichloromethane and distilled to obtain (S)-5-(amino methyl)-3-(3,4 difluorophenyl)oxazolidin-2-one. of formula-VII.

Step-f: acylation of (S)-5-(amino methyl)-3-(3,4-difluorophenyl)oxazolidin-2-one of formula-VII with Acetic anhydride yield the corresponding (S)—N-((3-(3,4-difluorophenyl)-2-oxooxazolidin-5-yl)methyl)acetamide of formula-VIII In this step (S)-5-(amino methyl)-3-(3,4-difluorophenyl) oxazolidin-2-one of formula-VII reacted with acetic anhydride in dichloromethane at 25-30° C., stirred for 3.0-4.0 hrs. After the completion of the reaction, organic layer is distilled and washed with water to obtain (S)—N-((3-(3,4-difluorophenyl)-2-oxooxazolidin-5-yl)methyl)acetamide of formula-VIII.

Step-g: Nitration of (S)—N-((3-(3,4-difluorophenyl)-2-oxooxazolidin-5-yl)methyl)acetamide with Nitrating Reagent (Nitric Acid & Sulphuric Acid) to Give (S)—N-((3-(4,5-difluoro-2-nitrophenyl)-2-oxooxazolidin-5-yl) methyl)acetamide of Formula IX This step involves addition of (S)—N-((3-(3,4-difluorophenyl)-2-oxooxazolidin-5-yl)methyl)acetamide to a solution of sulphuric acid and nitric acid in dichloromethane, stirred for 30.0 min at 0-5° C., stirred for 3.0-4.0 hrs. Then raised the temperature, separated organic layer and extracted with dichloromethane to obtain (S)—N-((3-(4,5-difluoro-2-nitrophenyl)-2-oxooxazolidin-5-yl) methyl)acetamide.

Step-h: (S)—N-((3-(4,5-difluoro-2-nitrophenyl)-2-oxooxazolidin-5-yl) methyl)acetamide Reacts with Morpholine to Give (S)—N-((3-(4-fluoro-5-morpholino-2-nitrophenyl)-2-oxooxazolidin-5-yl) methyl)acetamide Formula X In this step to a solution of (S)—N-((3-(4,5-difluoro-2-nitrophenyl)-2-oxooxazolidin-5-yl) methyl)acetamide in isopropyl alcohol, added morpholine, stirred for 1.0-2.0 hrs at 70-75° C. Then added water, separated and washed with water to obtain (S)—N-((3-(4-fluoro-5-morpholino-2-nitrophenyl)-2-oxooxazolidin-5-yl)methyl)acetamide.

Step-i: Reduction of (S)—N-((3-(4-fluoro-5-morpholino-2-nitrophenyl)-2-oxooxazolidin-5-yl) methyl)acetamide of Formula X to Give (S)—N-((3-(2-amino-4-fluoro-5-morpholinophenyl)-2-oxooxazolidin-5 yl)methyl)acetamide Formula XI In this step, reduction of (S)—N-((3-(4-fluoro-5-morpholino-2-nitrophenyl)-2-oxooxazolidin-5-yl)methyl)acetamide with Pd/C in methanol and maintaining at 5.0-6.0 Kg/Cm$^2$ of hydrogen gas for 3.0-4.0 hrs at 35-40° C. After completion of reaction filtered catalyst and distilled off solvent completely to obtain (S)—N-((3-(2-amino-4-fluoro-5-morpholinophenyl)-2-oxooxazolidin-5 yl)methyl)acetamide.

Step-j: Deamination of (S)—N-((3-(2-amino-4-fluoro-5-morpholinophenyl)-2-oxooxazolidin-5-yl) methyl)acetamide to Yield Desired (S)—N-((3-(4-fluoro-3-morpholinophenyl)-2-oxooxazolidin-5-yl) methyl)acetamide This step involves addition of Con. HCl to (S)—N-((3-(2-amino-4-fluoro-5-morpholinophenyl)-2-oxooxazolidin-5-yl)methyl)acetamide, maintaining the reaction mass at temperature 0-5° C. and then added sodium nitrite in water solution and stirred. After completion of the reaction, added hypo phosphorus ($H_3PO_2$) at below 10° C. and raised the reaction mass temperature to 30-35° C. After completion of reaction added dichloromethane and extracted with dichloromethane to obtain desired novel (S)—N-((3-(4-fluoro-3-morpholinophenyl)-2-oxooxazolidin-5-yl)methyl)acetamide.

The process described above for the preparation of novel oxazolidinone derivative compound [(S)—N-[[3-[4-fluoro-3-morpholino phenyl]-2-oxooxazolidin-5-yl] methyl] acetamide] of formula-I is further illustrated by the bellow given examples.

EXAMPLES

Example-1

Preparation of (R)-1-chloro-3-((3,4-difluorophenyl)amino)propan-2-ol of Formula-IV Taken 200.0 g of 3,4-difluoro nitro benzene, 600.0 ml of Toluene and 12.0 g of pd/C into autoclave at 25° C.-35° C. Apply the Hydrogen gas 2.0-6.0 Kg/Cm² and maintained the reaction for 3-4 hrs at 25° C.-35° C. Check the reaction mass TLC to conform reaction completion. After reaction complies unload the reaction mass and filter through hyflow bed and wash with toluene (200.0 ml). Take the filtrate and distilled under vacuum at below 50° C. the obtained 3,4-Difluoro aniline crude weight 152.0 g, Yield: 93.8%, purity by HPLC: 95.85%.

140.0 g of the previous step 3,4-Difluoro aniline, 120.4 g of (R)-Epichlorohydrine into a clean round bottom flask. slowly heat to 50° C.-55° C. and maintain the reaction mass for 5.0-6.0 hrs at 50° C.-55° C. and check the reaction mass TLC to conform reaction completion. After reaction compiles distill off low boilers under vacuum at below 50° C. to yield the crude compound of formula-III (170.0 g, yield: 71.0%, purity: 73.29%),

Example-2

Preparation of (R)-2-(3-((3,4-difluorophenyl)amino)-2-hydroxypropyl) isoindoline-1,3-dione (Formula-V)

Crude obtained from example-1 treated with 156.0 g of potassium phthalimide and 170.0 ml of DMF at 140-150° C. for 5.0-6.0 hrs. the reaction mass checked TLC to conform reaction completion. The reaction mass cooled to Room temperature, added 850.0 ml of water and 255.0 ml of methanol, stirred for 1.0-2.0 hrs at Room temperature. The filtered the solids, washed with mixture of water & methanol (170.0 ml). the dried the solids. The obtained solid weight 206.0 g, purity by HPLC: 63.1%.

Example-3

Preparation of (S)-2-((3-(3,4-difluorophenyl)-2-oxooxazolidin-5-yl)methyl)isoindoline-1,3-dione (Formula-VI)

410.0 g of (R)-2-(3-((3,4-difluorophenyl)amino)-2-hydroxypropyl) isoindoline-1,3-dione (formula-V), 820.0 ml of ethyl acetate and 210.0 g of CDI into Round bottom flask. Stirred for 3.0-4.0 hrs at room temperature. Checked reaction mass, TLC to conform reaction completion. After reaction complies, filtered the solids, washed with 205.0 ml of ethyl acetate. Then the wet cake and 1800.0 ml of water taken into a round bottom flask. Stirred for 1.0-2.0 hrs at 40-45° C., filtered the solids, washed with 410.0 ml of water. Dried the wet cake, the obtained of (S)-2-((3-(3,4-difluorophenyl)-2-oxooxazolidin-5-yl)methyl)isoindoline-1,3-dione, weight: 272.0 g, yield: 57.9%, purity by HPLC: 94.22%.

Example-4

Preparation of (S)—N-((3-(3,4-difluorophenyl)-2-oxooxazolidin-5-yl)methyl)acetamide (Formula-VIII)

370.0 g of (S)-2-((3-(3,4-difluorophenyl)-2-oxooxazolidin-5-yl)methyl)isoindoline-1,3-dione, 370.0 ml of methanol and 1480.0 ml of water, 216.5 g of hydrazine hydrate into a round bottom flask at room temperature. The reaction mass slowly heated to 65-70° C., stirred for 2.0-3.0 hrs same temperature. Checked reaction mass TLC to conform reaction completion. After reaction complete, cooled the reaction mass to room temperature, extracted product with dichloromethane. The organic layer distilled off completely to give the crude of formula-VII (208.0 g), Crude obtained above was added 370.0 ml of dichloromethane, 147.5 g of acetic anhydride added slowly above to the reaction mass at 25-30° C., stirred for 3.0-4.0 hrs, checked reaction mass TLC to conform reaction completion. After reaction complies, wash the reaction mass with water. The organic layer distilled off completely to get obtained crude mass to this mass 370.0 ml of water was added under stirring maintain for 1 hr and filtered the solid, washed with water. Dried to get the (S)—N-((3-(3,4-difluorophenyl)-2-oxooxazolidin-5-yl)methyl)acetamide Formula-VIII, weight: 230.0 g, yield: 81.6%, purity by HPLC: 95.54%.

Example-5

Preparation of (S)—N-((3-(4-fluoro-5-morpholino-2-nitrophenyl)-2-oxooxazolidin-5-yl)methyl)acetamide (Formula-X)

320.3 g of sulphuric acid into round bottom flask. Cooled to 0-5° C., slowly added 88.7 g of nitric acid at 0-5° C., stirred for 30 min, added 850.0 ml of dichloromethane. Then added 170.0 g of (S)—N-((3-(3,4-difluorophenyl)-2-oxooxazolidin-5-yl)methyl)acetamide lot wise at 0-5° C. stirred for 30.0 min at 0-5° C. raised the reaction mass temperature to room temperature. Stirred for 3.0-4.0 hrs. checked TLC to conform reaction completion. After reaction complies, the reaction quenched into 850.0 ml of chilled water, separated organic layer. Extracted aqueous layer with dichloromethane. The combined organic layer distilled off solvent. Crude compound (S)—N-((3-(4,5-difluoro-2-nitrophenyl)-2-oxooxazolidin-5-yl) methyl) acetamide of formula IX. (182.0 g)

To the crude thus obtained was added_182.0 ml of isopropyl alcohol and to this 122.4 g of Morpholine was added slowly and stirred for 1.0-2.0 hrs at 70-75° C. TLC was checked to conform reaction completion. Once complies, added 340.0 ml of water to the reaction mass, then cooled to room temperature. The material thus separated was filtered and washed with 170.0 ml of water. Dried to get the product obtained (S)—N-((3-(4-fluoro-5-morpholino-2-nitrophenyl)-2-oxooxazolidin-5-yl)methyl)acetamide of formula-X, weight: 189.0 g, yield: 78.68%, purity by HPLC: 91.12%.

Example-6

Preparation (S)—N-((3-(2-amino-4-fluoro-5-morpholinophenyl)-2-oxooxazolidin-5-yl)methyl) acetamide (Formula-XI)

100.0 g of (S)—N-((3-(4-fluoro-5-morpholino-2-nitrophenyl)-2-oxooxazolidin-5-yl)methyl)acetamide, 1500.0 ml of methanol and 10.0 g of Pd/C are subjected to hydrogenation in an autoclave. At 5.0-6.0 Kg/Cm² of hydrogen gas maintain for 3.0-4.0 hrs at 35-40° C. Check for reaction completion by TLC. After reaction complies, filtered the catalyst and distilled off solvent completely. The obtained (S)—N-((3-(2-amino-4-fluoro-5-morpholinophenyl)-2- oxoozazolidin-5-yl)methyl) acetamide formula-XI, weight: 80.0 g, yield: 86.9%, purity by HPLC: 96.32%.

Example-7

Preparation (S)—N-((3-(4-fluoro-3-morpholinophenyl)-2-oxoozazolidin-5-yl)methyl)acetamide (Formula-I)

To 82.0 ml of Con.HCl slowly added 80.0 g of (S)—N-((3-(2-amino-4-fluoro-5-morpholinophenyl)-2-oxoozazolidin-5-yl)methyl) acetamide (Formula-XI) maintaining reaction mass temperature 0-5° C. To this were added 23.5 g of sodium nitrite in 125.0 ml of water solution at 0-5° C., stirred for 30 min, checked TLC to conform reaction completion. Once complies added 22.5 g of hypo phosphorus ($H_3PO_2$) at below 10° C., then raised the reaction mass temperature to 30-35° C., stirred for 30 min and checked TLC to conform reaction completion. After reaction complies, cooled the reaction mass to 0-5° C., added 400.0 ml of dichloromethane and adjusted pH to 7.0-8.0 with 48% of caustic lye. Separated organic layer and aqueous layer extracted with dichloromethane. Combined organic layer, was distilled off to get the crude. Which is then purified by column chromatography and further re-crystallized with methanol to give (S)—N-((3-(4-fluoro-3-morpholinophenyl)-2-oxoozazolidin-5-yl)methyl)acetamide formula-I, weight: 10.0 g, yield: 13.0%, purity by HPLC: 99.5%. The structure conformed by $^1$H-NMR, $C^{13}$-NMR, Mass, IR spectral data.

The structural elucidation of the compound of formula I is confirmed by $^1$H-NMR, C13-NMR, Mass, IR spectral data etc. stated as below:

IR Spectral Data:
3335, 3085, 2984, 2900, 2743, 2697, 1736, 1671, 1609, 1597, 1542, 1512, 1474, 1420, 1369, 1348, 1318, 1285, 1231, 1142, 1114, 1083. (Fig-I)

(H-NMR:$CDCl_3$: δ 2.01 (s, 3H), 3.06 (t, 4H), 3.60-3.78 (m, 4H), 3.85-3.86 (t, 2H), 4.03 (t, 2H), 4.78 (m, 1H), 6.12 (s, 1H), 6.82-6.85 (m, 1H), 6.98-7.03 (q, 1H), 7.32-7.34 (dd, 1H) (Fig.-II)

$^{13}$C-NMR:$CDCl_3$: 22.7, 41.7, 47.7, 50.5, 66.6, 71.8, 109.6, 111.9, 116.2, 134.3, 139.9, 140.0, 150.8, 153.2, 154.6, 171.2. (Fig-III)

ESI-MS (m/z): 338.37 (M+1); (Fig-IV)

The compound of formula-I is further characterized by XRD spectrum of 8.898, 13.05, 13.799, 15.849, 18.817, 19.138, 19.454, 20.193, 21.395, 21.686, 22.289, 22.833, 23.504, 26.133 and 32.448 degrees 2 theta. (as shown in FIG. 5).

Method of XRD Analysis:
Powder XRD Make: Bruker D2 Phaser
LD Samples Data Collected Using PMMA Holder and Scan Parameter Details as Follows:
Two theta range: 3-40°
Step size: 0.012
Time for step: 72 s
Generator KV: 30
Generator mA: 10
Detector: Lynx Eye
Spinner: 15 rpm
X-Ray source: Cu Kα
Antimicrobial Study To ascertain the antibacterial activities of the compound-I, a thorough antimicrobial study was performed and its coverage spectrum as well as bacteriostatic and bactericidal activities were studied.

Anti bacterial evaluation of compound-I was done against *Stenotrophomonas maltophilia* on following parameters— f. Agar-plate assay for different concentrations (10, 50, 100, 150 µg)
g. MIC studies
   1. With different concentrations (1000 to 5 µg/ml—~10 different concentrations)
   2. Different time periods (4 to 32 hrs—8 different time intervals)
h. Mode of action with relation to survivability of organism
   1. Cidal/static with concentration and incubation time based)
   2. Evaluation by colony counting/dye based
i. Susceptibility test (evaluation of >40 antibiotics of different nature)
j. Antibacterial potential studies with other infectious bacteria (~20 different strains)

Results

Agar-Plate Assay

Agar plate assay was performed to assess quickly the antibacterial nature of compound-I using *Stenotrophomonas maltophilia*, a known causative microbial strain for pulmonary diseases, nosocomial infections, co-morbid illness, bacteremia, meningitis, endocarditis, etc.

Figure 6:
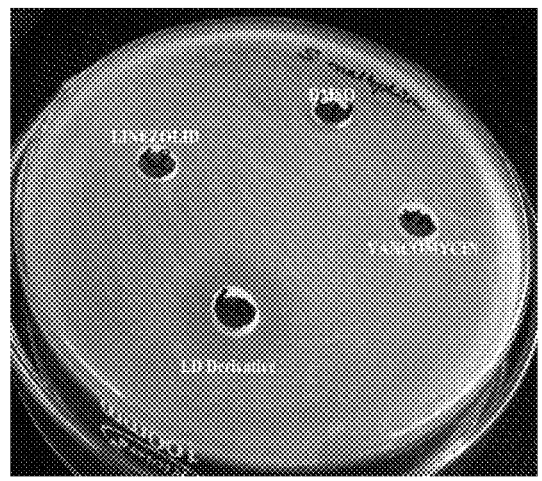
FIG. 6 is Agar plate assay for Oxazolidinone compound of formula-I.

In view of the background information provided, the initial agar plate based antibacterial property of compound-I, vancomycin and linezolid was evaluated against *S. maltophilia* using agar plates and 50 µg of each compound dissolved in DMSO solution. To nullify the effect of DMSO if any on *S. maltophilia*, DMSO also used as test compound and the data presented in Table 1 and FIG. 6.

TABLE 1

Antimicrobial activity of compound-I against *Stenotrophomonas maltophilia*

| S. No | Compound | Zone of growth inhibition in mm |
|---|---|---|
| 1 | Vancomycin | 00 |
| 2 | Linezolid | 00 |
| 3 | LDD-01/2013 | 17 |
| 4 | DMSO | 00 |

It is clear from above table that the growth of *S. maltophilia* was inhibited by only compound-I but not by either vancomycin or linezolid suggesting that compound-I has potential in health sector.

Compound-I Concentration Based Growth Inhibition Studies

It is important to understand the antibacterial efficiency of compound-I before initiating further investigations. To evaluate the same, 0 to 250 µg concentration range used for agar plate assay. Two percent agar plates were prepared and 24 hours grown *S. maltophilia* was spread on agar plate and incubated at 4° C. After 30 min, the agar plates consisting of *S. maltophilia* were brought to sterile environment at room temperature and using sterile borer wells were developed. In each well, a known concentration of compound-I dissolved in DMSO was added. After 24 hours of incubation at 37° C., the zone of inhibition was measured. The data presented in Table 2 and FIG. 7.

TABLE 2

Antimicrobial activity of different concentrations of
compound-I against *Stenotrophomonas maltophilia*

| S. No | Compound-I Conc. (µg/ml) | Zone of growth inhibition in mm |
|---|---|---|
| 1 | 00 | 00 |
| 2 | 10 | 16 |
| 3 | 50 | 17 |
| 4 | 100 | 18 |
| 5 | 150 | 20 |
| 6 | 200 | 20 |
| 7 | 250 | 22 |

Figure 7:
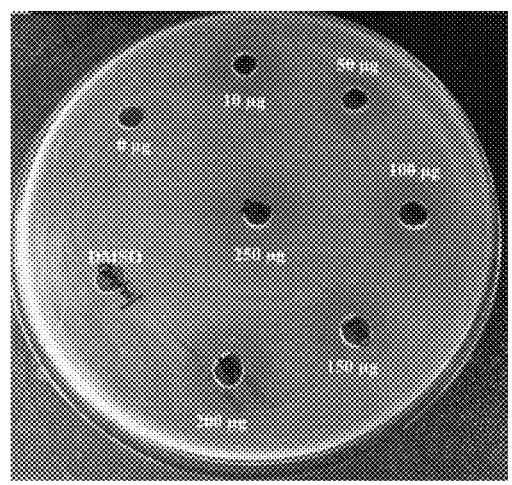
FIG. 7 is Agar plate showing the zone of inhibition of *S. maltophilia* against compound-I

The data presented in Table 2 and FIG. 7 clearly denote that
  i. At 10 µg level the compound-I is effective in growth inhibition of *S. maltophilia*.
  ii. Increase of compound-I concentration resulted in increased zone of growth inhibition.
  iii. Proportionate growth inhibition zone was not noticed with increase of compound-I concentration on agar plate assay.

The above data is interesting especially with respect to low dose is sufficient to reduce the growth of *S. maltophilia*. However, the observation of un-proportionate inhibition zone Vs concentration of compound-I is appealing fact. This may attributed to mass transfer of compound-I in agar during experimentation which influences the drug and microbial interaction. One of the alternatives to reduce the influence of mass transfer and improve the contact between compound-I and microbial strain was removal of solid barrier or increasing the diffusion of compound in the medium by broth dilution method.

MIC Studies

In microbiology, minimum inhibitory concentration (MIC) is the lowest concentration of an antimicrobial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents. A MIC is generally regarded as the most basic laboratory measurement of the activity of an antimicrobial agent against an organism. In this method the above problem of diffusion is also eliminated.

MIC of Compound-I by Tube Dilution Method

To find out the MIC of compound-I concentration required for inhibition of *S. maltophilia* growth, ten different concentrations of compound-I ranging from 0 to 1000 µg/ml (1000, 500, 250, 125, 62.5, 31.25, 15.62, 7.81, 3.90 and 0 µg/ml) was supplemented in one ml of sterile medium containing $10^7$ cells. These tubes were incubated at 37° C. The growth of the *S. maltophilia* was observed after 12 hours. The data presented in the FIG. 8.

Figure 8:
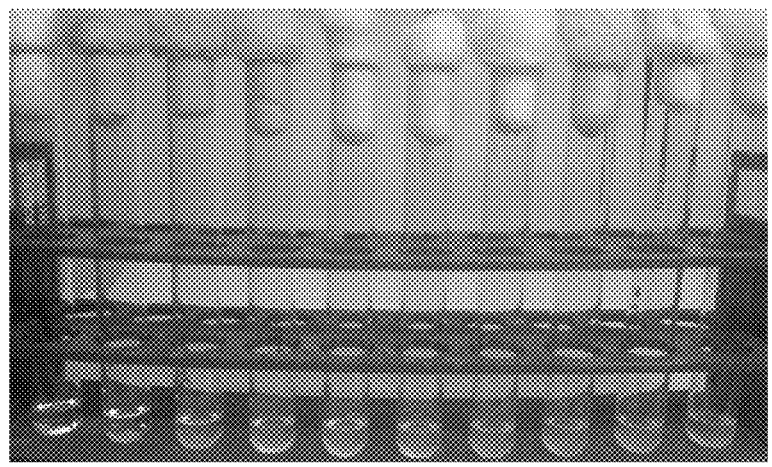
FIG. 8 is MIC of compound-I by tube dilution method 12 hours.

It is clear from FIG. 8 that the growth of *S. maltophilia* noticed in all studied concentrations ranging from 0 to 250 µg/ml however, the growth visibility varied with the concentration of compound-I. In tubes supplemented with 500 and 1000 µg/ml of compound-I, no growth was observed suggesting for this compound MIC is 500 µg with respect to *S. maltophilia*.

MIC at Different Time Periods

Though the MIC for LD derivate against *S. maltophilia* is 500 µg/ml, with the time of incubation the growth of *S. maltophilia* may differ due to metabolic nature of the microbe or physiological properties of the compound. Keeping this in view, the growth was monitored visually at different time intervals. The data is presented as supplement at the end of the report. It is evident from the figures that four hour incubation did not show any growth in any tube supplemented with compound-I at different concentration. However, with the increase in time from four to eight hours, the growth of *S. maltophilia* could be seen in the tubes supplemented with 62.5, 31.25, 15/62, 7.81, 3.90 and 0 concentration of compound-I. Further increase in incubation time beyond 12 hours i.e. 16, 20 and 24 hours, the growth of *S. maltophilia* could be visualized in all tubes except 500 and 1000 µg supplemented tubes. This denotes that 500 µg compound-I is effective in inhibiting the growth *S. maltophilia* in 12 hours.

Mode of Action with Relation to Survivability of Organism Cidal/Static

To evaluate the growth inhibition property of compound-I is associated with killing or arresting the growth of *S. maltophilia*, the growth pattern of organism in presence of different concentrations of compound-I with respect to incubation time was analyzed. The results were tabulated. It was evident from the data that in any given concentration of compound-I, the growth was not detected till 4 hours of incubation. With the increase in incubation time beyond 4 hours, visible growth was not observed till 16 hours incubation in 62.5, 125 and 250 µg/ml supplemented tubes, however, further extension of growth periods i.e., beyond 20 hours, the growth of *S. maltophilia* was noticed. This suggests that growth of this organism was temporarily arrested and organism could regain the growth whereas supplementation of compound-I in concentrations of 500 µg/ml and beyond, the growth of *S. maltophilia* was not observed even after 120 hours. This data further confirm that compound-I is effective in eradicating the *S. maltophilia* if used 500 µg/ml. In addition the data also suggest at 500 µg/ml and above concentration, the compound-I act as bactericidal and below 500 µg/ml it may act as bacteriostatic.

TABLE 3

MIC of the compound-I against *Stenotrophomonas maltophilia* with respect to time

| S. No | Time (hrs) | Bacteriostatic µg/ml | Bacteriocidal µg/ml |
|---|---|---|---|
| 1 | 0 | NA | NA |
| 2 | 4 | ND | ND |
| 3 | 8 | 62.5 | — |
| 4 | 12 | 125 | — |
| 5 | 16 | 250 | — |
| 6 | 20 | — | 500 |
| 7 | 24 | — | 500* |

Figure 9:
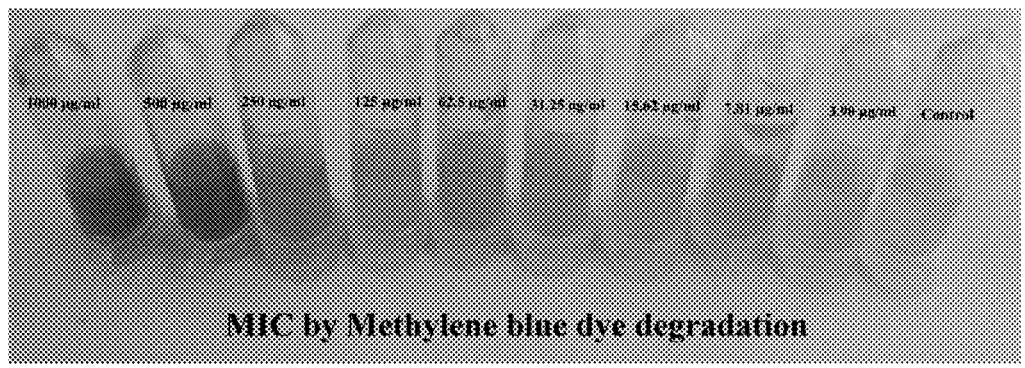
FIG. 9 is Dye based evaluation of cidal/static nature of compound-I to *S. Maltophilia

*Note:
No growth was observed in 500 µg/ml supplemented conditions up to 10 days Dye Based Analysis The antibacterial nature of compound-I has been further confirmed by dye interactive method. The FIG. 9 indicates the survivability nature of *S. maltophilia* in the presence of compound-I. It was clear from the FIG. 9 that supplementation of methylene blue to the *S. maltophilia* cultures grown in presence of different concentrations of compound-I, the blue colour was noticed with cultures supplemented with 500 and 1000 µg/ml and remaining cultures did not show blue colour. The basic principle associated with the colour change or disappear of blue colour is associated with reducing environment. Methylene blue solution is blue when in an oxidizing environment, but will turn colorless if exposed to a reducing agent. Growth of any living organism is associated with wide range chemical reactions known as metabolism, basically characterized with redox reactions and several reducing cofactors are always exists in actively growing cells. Hence, exposure of methylene blue to such reducing environment (living organism), the dye immediately reduced and losses its colour. Since methylene blue colour is disappeared in the S. maltophilia culture tubes supplemented up to the concentration of 250 µg/ml compound-I, it denote that compound-I concentration at 500 µg/ml or above is detrimental for growth of S. maltophilia.

Figure 10:
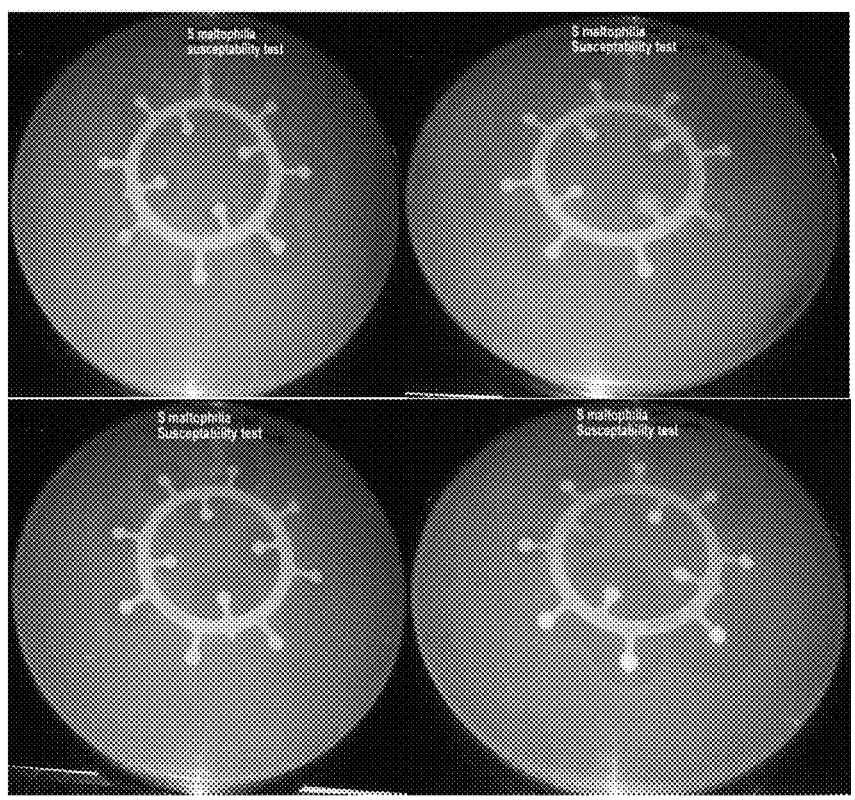
*
FIG. 10 is Agar plates indicating the antimicrobial profile of *S. maltophilia* for commercially available antibiotics

Susceptibility Test Profile of S. maltophilia for Different Antibiotics (FIG. 10)

TABLE 4

Antimicrobial profile of S. maltophilia for commercially available antibiotics

| S. No | Antibiotic | Quantity in µg | Zone (mm) |
|---|---|---|---|
| 1. | Azithromycin | 30 | 12 |
| 2. | Rifampicin | 5 | 3 |
| 3. | Penicillin | 10 | 6 |
| 4. | Piperacillin | 100 | 8 |
| 5. | Augmentin | 30 | 7 |
| 6. | Ampicillin/sulbactam | 10/10 | 12 |
| 7. | Roxithromycin | 30 | 4.5 |
| 8. | Erythromycin | 15 | 4 |
| 9. | Ampicillin | 10 | 6.5 |
| 10. | Cloxacillin | 1 | 3 |
| 11. | Amoxycillin | 10 | 6.5 |
| 12. | Vancomycin | 30 | 6.5 |
| 13. | Chloramphenicol | 30 | 11 |
| 14. | Ciprofloxacin | 5 | 12 |
| 15. | Norfloxacin | 10 | 9 |
| 16. | Lincomycin | 2 | Resistant |
| 17. | Lomefloxacin | 30 | 12 |
| 18. | Clindamycin | 2 | Resistant |
| 19. | Tetracycline | 30 | 6 |
| 20. | Levofloxacin | 5 | 15 |
| 21. | Pefloxacin | 5 | 9 |
| 22. | Sparfloxacin | 5 | 17 |
| 23. | Ofloxacin | 5 | 11 |
| 24. | Doxycycline | 30 | 8 |
| 25. | Gentamicin | 10 | 7 |
| 26. | Netillin(Netilmicin sulphate) | 30 | 7 |
| 27. | Nalidixic | 30 | 7 |
| 28. | Kanamycin | 30 | 3 |
| 29. | Amikacin | 30 | 8 |
| 30. | Co-Trimoxazole | 25 | 10 |
| 31. | Tobramycin | 10 | 10 |
| 32. | Clarithromycin | 15 | Resistant |
| 33. | Nitrofurantoin | 300 | 7 |
| 34. | Streptomycin | 10 | 12 |
| 35. | Oxytetracycline | 30 | 2 |
| 36. | Furazolidone | 50 | Resistant |
| 37. | Augmentin | 30 | 8 |
| 38. | Gatifloxacin | 5 | 15 |
| 39. | Carbenicillin | 100 | 14 |
| 40. | Lome floxacin | 10 | 14 |
| 41. | Imipenem | 10 | 6 |
| 42. | Teicoplanin | 30 | 4 |
| 43. | Cefepime | 30 | 9 |
| 44. | Cefaloridine | 30 | 7 |
| 45. | Tobramycin | 10 | 9 |

Antibacterial Potential Studies with Other Infectious Bacteria (~20 Different Strains)

To understand the antimicrobial potential of compound-I, initial experiments were planned to evaluate comparative microbial growth inhibition zone against Linezolid and Vancomycin using twenty different bacterial strains consisting of gram-positive and gram-negative nature. The selection of vancomycin for comparison was based on the fact it is an alternative antibiotic that is generally used for treating the gram-positive bacterial infections. The results are reported in Table 5.

TABLE 5

Antimicrobial activity of compound-I with other microorganisms (Zone of growth inhibition in mm)

| S. No | Strains | Compound-I | Linezolid | Vancomycin |
|---|---|---|---|---|
| 1 | M. luteus | 12 | 45 | 32 |
| 2 | B. sterothemophilus | 00 | 00 | 00 |
| 3 | S. maltophilla | 17 | 00 | 00 |
| 4 | P. putida | 00 | 00 | 00 |
| 5 | K. pneumonia | 00 | 35 | 25 |
| 6 | P. aeruginosa | 12 | 00 | 00 |
| 7 | E. coli | 12 | 35 | 25 |
| 8 | P. vulgaris | 00 | 00 | 00 |
| 9 | S. typhi | 00 | 40 | 14 |
| 10 | B. subtilis | 12 | 40 | 25 |
| 11 | S. mutans | 00 | 40 | 30 |
| 12 | B. sphaericus | 00 | 30 | 12 |
| 13 | B. circulans | 00 | 38 | 27 |
| 14 | Lysinobacillus | 00 | 40 | 30 |
| 15 | B. cereus (1) | 17 | 00 | 00 |
| 16 | B. megatherium | 12 | 37 | 27 |
| 17 | B. cereus (2) | 00 | 35 | 27 |
| 18 | P. mirabilis | 00 | 35 | 27 |
| 19 | B. cereus (3) | 00 | 45 | 32 |
| 20 | S. paratyphi | 00 | 00 | 25 |

Among all tested different microbial strains, S. maltophilia, P. aeruginosa and one of the strains of B. cereus showed anti bacterial activity against compound-I but not vancomycin or Linezolid suggesting compound-I could be a potential drug candidate to control the infections associated with above organisms more effectively.

Conclusions:

A brief summary of the Antimicrobial activity of Compound-I is given below:
  Compound-I is active against S. Maltophilia as against other antibiotics like Linezolid and Vancomycin which were unable to inhibit the growth.
  Concentration based antimicrobial activity tests have shown that at 10 µg level the Compound-I is effective in growth inhibition of S. Maltophilia
  MIC studies suggested that Compound-I at 500 µg/ml and above is effective for complete inhibition of S. Maltophilia.
  The 500 µg of Compound-I is effective in inhibiting the growth S. Maltophilia in 12 hours
  At 500 µg/ml and above concentration, the Compound-I act as bactericidal and below 500 µg/ml it may act as bacteriostatic.
  The antibiotic susceptibility profile of S. Maltophilia was explored
  Compound-I is effective against Xanthomonadaceae (S. maltophilia and pseudomonas sp.) & some species of Bacillus (Bacillus cereus) family members.
  The preliminary tests for Single Dose Acute Toxicity of Compound-I was conducted in Wistar rat at USFDA approved Teena Laboratories, Hyderabad, as per the protocol schedule Y of Drugs & Cosmetic Act and Rules. The results of Single Dose Acute Toxicity are as below:
  No significant treatment related effect on food intake: body weight and clinical signs were observed in all animals.
  There were no pre-terminal deaths observed in vehicle control, low dose, middle dose and high dose group animals in single dose toxicity study.

Haematological parameters in all groups of animals at three dose levels were found to be in normal range when compared with control animals.

Biochemical parameters in all groups of animals at three dose levels were found to be in normal range when compared with control animals.

The study established that Compound-I has not produced any significant changes in clinical, behavioral, physical, physiological, biochemical, haematological parameters at three different dose levels on administration test item at recommended clinical dosage schedule under experimental conditions in the animal studies.

Thus the single dose toxicity study in Wistar rats did not show any mortality after administration of Compound-I test item once with low intermediate and High dosage i.e. 45.0 mg/kg, 225.0 mg/kg and 450 mg/kg and revealed that no significant changes occurred in physical and physiological parameters under experimental conditions in Wistar rat.

The invention therefore provides novel oxazolidinone compound-I for therapeutic use as a potential antibacterial drug against Multi-Drug Resistant *S. Maltophilia* pathogen and a large number of gram positive and gram negative pathogens.

The compound-I can be further converted in pharmaceutically acceptable salts, hydrates, solvates and other pharmaceutically suitable derivatives for use in a pharmaceutical compositions and pharmaceutical preparation. In some embodiments, enantiomers of the compound-I can also be prepared for being suitably used in the industry.

Pharmaceutically acceptable salts include salts prepared from inorganic or organic bases and Inorganic or organic acids.

Wherein Salts derived from inorganic bases include luminium, ammonium, calcium, copper, ferric, ferrous, lithium, magnesium, manganic salts, manganous, potassium, sodium, zinc and the like. Salts in the solid form may exist in more than one crystal structure, and may also be in the form of hydrates. Salts derived from non-toxic organic bases include salts of primary, secondary and tertiary amines, substituted amines including naturally occurring substituted amines, cyclic amines and basic ion exchange resins, such as arginine, betaine, caffeine, choline, N,N-dibenzylethylene-diamine, diethylamine, 2-diethylaminoethanol, 2-dimethylethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from the pharmaceutically acceptable non-toxic acids including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulphuric, tartaric, p-toluenesulfonic acid and the like.

The pharmaceutical compositions of the compound of Formula I may be prepared by combining the compound or its pharmaceutically acceptable salt with a solid or liquid pharmaceutically acceptable carrier or with pharmaceutically acceptable adjuvants and excipients conventionally used for this purpose.

The pharmaceutical compositions may be in the forms of solids or liquids such as powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. The liquid pharmaceutical compositions may be solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical compositions may be provided in unit dosage forms containing effective amounts of the active ingredient (compound of Formula-I).

The quantity of active ingredient (compound of Formula I) may be varied or adjusted depending upon the particular application, the potency of the particular compound, the desired concentration in the pharmaceutical compositions and unit dosage forms. Generally, the quantity of active component may be any appropriate value between 0.1% to 99% by weight of the composition.

In a therapeutic use, the compounds or pharmaceutical compositions may be administered orally, parenterally and/or topically to obtain and maintain a blood concentration of the active component which will be antibacterially effective. Generally, such antibacterially effective amount of dosage of active component will be in the range of about 1 µg to about 100 mg/kg of body weight/day. However, the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula-I may also be administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt dissolved in a pharmaceutically acceptable liquid carrier such as, for example, water-for-injection and a buffer to provide a suitably buffered isotonic solution, for example, having a pH of about 3.5-7. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of Formula I according to this invention are advantageously administered orally in solid and liquid dosage forms.

As a topical treatment an effective amount of Formula I may be admixed in a pharmaceutically acceptable gel or cream vehicle that can be applied to the patient's skin at the area of treatment. Preparation of such creams and gels is well known in the art and can include penetration enhancers.

We claim:

1. An oxazolidinone antibacterial compound [(S)—N-[[3-[4-fluoro-3-morpholino phenyl]-2-oxooxazolidin-5-yl] methyl] acetamide] of formula-I, a pharmaceutically acceptable salt, solvate, or hydrate thereof

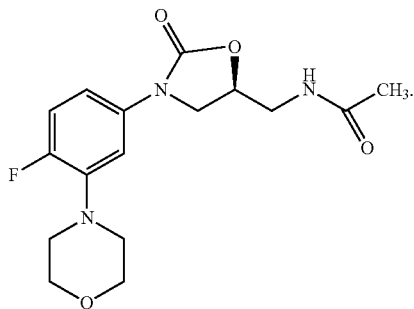

Compound-I

2. The oxazolidinone compound of claim 1, having an IR spectral data of 3335 cm$^{-1}$, 3085 cm$^{-1}$, 2984 cm$^{-1}$, 2900 cm$^{-1}$, 2743 cm$^{-1}$, 2697 cm$^{-1}$, 1736 cm$^{-1}$, 1671 cm$^{-1}$, 1609 cm$^{-1}$, 1597 cm$^{-1}$, 1542 cm$^{-1}$, 1512 cm$^{-1}$, 1474 cm$^{-1}$, 1420 cm$^{-1}$, 1369 cm$^{-1}$, 1348 cm$^{-1}$, 1318 cm$^{-1}$, 1285 cm$^{-1}$, 1231 cm$^{-1}$, 1142 cm$^{-1}$, 1114 cm$^{-1}$, 1083 cm$^{-1}$.

3. The oxazolidinone compound of claim 1, having an H-NMR:CDCl$_3$ of δ2.01 (s, 3H) ppm, 3.06 (t, 4H) ppm, 3.60-3.78 (m, 4H) ppm, 3.85 3.86 (t, 2H) ppm, 4.03 (t, 2H) ppm, 4.78 (m, 1H) ppm, 6.12 (s, 1H) ppm, 6.82-6.85 (m, 1H) ppm, 6.98 7.03 (q, 1H) ppm, 7.32-7.34 (dd, 1H) ppm.

4. The oxazolidinone compound of claim 1, having an $^{13}$C-NMR:CDCl$_3$ of 22.7 ppm, 41.7 ppm, 47.7 ppm, 50.5 ppm, 66.6 ppm, 71.8 ppm, 109.6 ppm, 111.9 ppm, 116.2 ppm, 134.3 ppm, 139.9 ppm, 140.0 ppm, 150.8 ppm, 153.2 ppm, 154.6 ppm, 171.2 ppm.

5. The oxazolidinone compound of claim 1, having an ESI-MS (m/z) of 338.37 (M+1).

6. The oxazolidinone compound of claim 1, having an XRD spectrum having principal peaks at 8.898, 13.05, 13.799, 15.849, 18.817, 19.138, 19.454, 20.193, 21.395, 21.686, 22.289, 22.833, 23.504, 26.133 and 32.448 degrees 2 theta.

7. A process for the preparation of an oxazolidinone compound (S)—N-((3-(4-fluoro-3-morpholinophenyl)-2-oxooxazolidin-5-yl)methyl)acetamide of formula-I

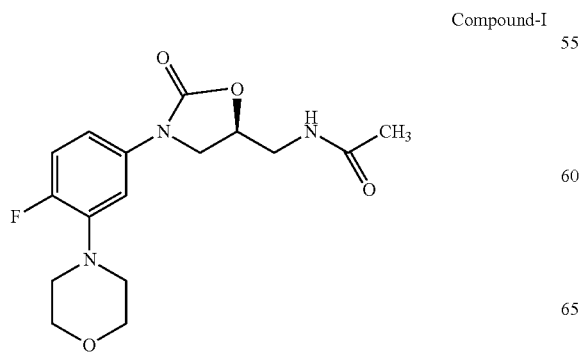

Compound-I comprising the steps of:

a) reduction of 3,4-difluoro nitrobenzene compound of formula-II

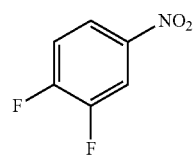

Compound-II to give 3,4-difluoro-aniline compound of formula-III;

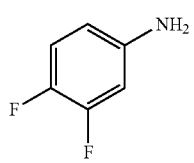

Compound-III b) reacting compound-III with (R) epichlorohydrin to obtain (R)-1-chloro-3-((3,4-difluorophenyl)amino)propan-2-ol compound of formula-IV;

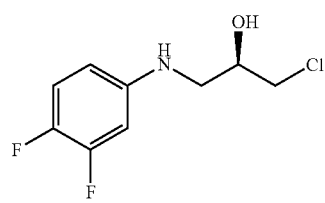

Compound-IV c) coupling the (R)-1-chloro-3-((3,4-difluorophenyl) amino)propan-2-ol compound of formula-IV with Potassium phthalimide to obtain (R)-2-(3-((3,4-difluorophenyl)amino)-2-hydroxyl propyl)isoindoline-1,3-dione compound of formula-V;

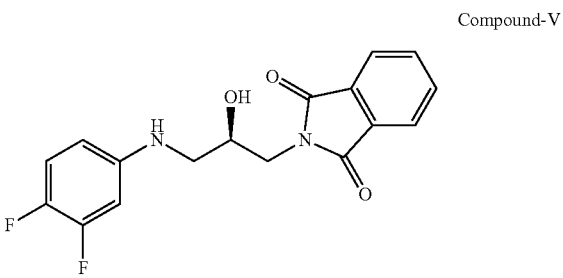 [SMILES: O=C1c2ccccc2C(=O)N1C[C@H](O)CNc1ccc(F)c(F)c1]

Compound-V d) cyclization of (R)-2-(3-((3,4-difluorophenyl)amino)-2-hydroxyl propyl) isoindoline-1,3-dione compound of formula-V with CDI to obtain (S)-2-((3-(3,4-difluorophenyl)-2-oxooxazolidin-5-yl)methyl)isoindoline-1,3-dione compound of formula-VI;

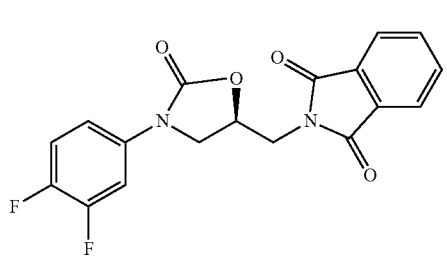

Compoud-VI e) opening of phthalimide ring of compound-VI by reacting with Hydrazine hydrate to obtain (S)-5-(amino methyl)-3-(3,4-difluorophenyl)oxazolidin-2-one compound of formula-VII;

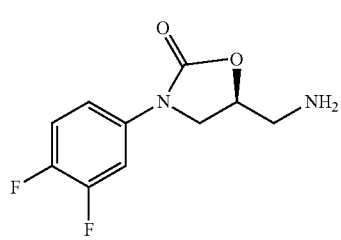

Compound-VII f) acylation of compound-VII with Acetic anhydride to obtain the corresponding (S)—N-((3-(3,4-difluorophenyl)-2-oxooxazolidin-5-yl)methyl)acetamide compound of formula-VIII;

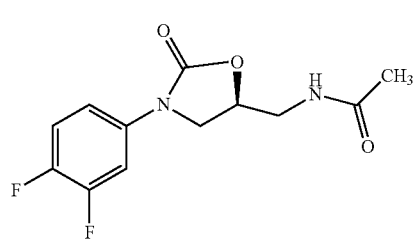

Compound-VIII g) nitration of compound VIII with the nitrating reagents nitric acid & sulphuric acid to give (S)—N-((3-(4,5-difluoro-2-nitrophenyl)-2-oxooxazolidin-5-yl) methyl) acetamide compound of formula IX;

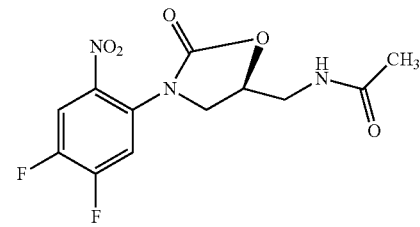

Compound-IX h) reacting (S)—N-((3-(4,5-difluoro-2-nitrophenyl)-2-oxooxazolidin-5-yl) methyl) acetamide compound-IX with morpholine to give (S)—N-((3-(4-fluoro-5-morpholino-2-nitrophenyl)-2-oxooxazolidin-5-yl)methyl)acetamide compound formula-X;

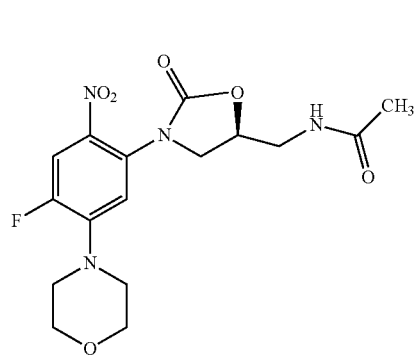

Compound-X i) reduction of (S)—N-((3-(4-fluoro-5-morpholino-2-nitrophenyl)-2-oxooxazolidin-5-yl)methyl)acetamide compound of formula-X to obtain (S)—N-((3-(2-amino-4-fluoro-5-morpholinophenyl)-2-oxooxazolidin-5-yl)methyl)acetamide formula XI;

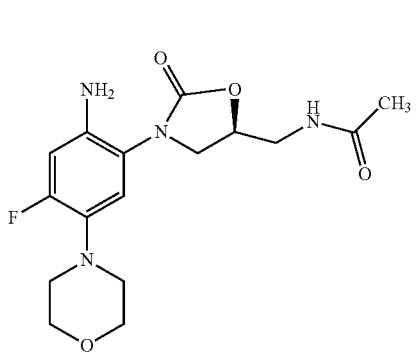

Compound-XI j) deamination of (S)—N-((3-(2-amino-4-fluoro-5-morpholinophenyl)-2-oxooxazolidin-5-yl)methyl)acetamide (compound-XI) to obtain (S)—N-((3-(4-fluoro-3-morpholinophenyl)-2-oxooxazolidin-5-yl)methyl)acetamide compound of formula-I

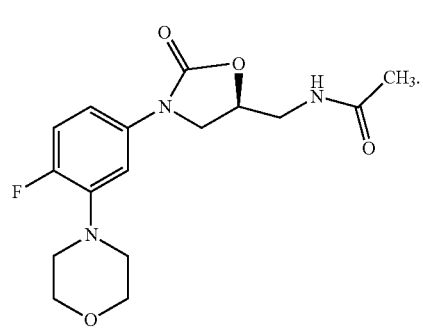

Compound-I

8. An enantiomerically pure compound of formula-1 as claimed in claim 1.

9. An enantiomerically pure compound of formula-1 obtained by the process as claimed in claim 7.

10. A pharmaceutical composition comprising a pharmaceutically acceptable carrier and the oxazolidinone compound-I or its pharmaceutically acceptable salt thereof as claimed in claim 1.

11. A pharmaceutical composition as claimed in claim 10, wherein the composition comprises the compound of formula-I in an amount between 0.1% to 99% by weight of the composition.

12. A formulation comprising the pharmaceutical composition as claimed in claim 11.

13. A formulation as claimed in claim 12, wherein said formulation comprises compound of formula-I in amount of about 1 µg to about 100 mg/kg of body weight/day.

* * * * *

UNITED STATES PATENT AND TRADEMARK OFFICE
CERTIFICATE OF CORRECTION

PATENT NO.       : 9,573,910 B2                          Page 1 of 1
APPLICATION NO.  : 15/034878
DATED            : February 21, 2017
INVENTOR(S)      : Raghu Mitra Alla et al.

It is certified that error appears in the above-identified patent and that said Letters Patent is hereby corrected as shown below:

In the Claims

Column 27, Line 35, Claim 3, delete "3.85 3.86" and insert -- 3.85-3.86 --

Column 27, Line 37, Claim 3, delete "6.98 7.03" and insert -- 6.98-7.03 --

Column 29, Line 51, Claim 7, delete "-yl) methyl)" and insert -- -yl)methyl) --

Column 29, Line 67, Claim 7, delete "-yl) methyl)" and insert -- -yl)methyl) --

Signed and Sealed this
Twenty-fifth Day of April, 2017

Michelle K. Lee
*Director of the United States Patent and Trademark Office*